United States Patent [19]
Vo et al.

[11] Patent Number: 5,640,220
[45] Date of Patent: Jun. 17, 1997

[54] APPARATUS AND METHOD FOR DETERMINING CHARACTERISTICS OF A HUMAN RETINA USING ENTOPTICALLY OBSERVED LEUKOCYTES AND OTHER PSYCHOPHYSICAL PHENOMENONA

[76] Inventors: Van Toi Vo, 34 Bridge St., Lexington, Mass. 02173; Jianguo Sun, 4719 Lolly Dr., Monroeville, Pa. 15146

[21] Appl. No.: 419,150

[22] Filed: Apr. 10, 1995

[51] Int. Cl.$^6$ .............................. A61B 3/10; A61B 3/14; A61B 5/02

[52] U.S. Cl. .................... 351/213; 351/206; 351/215; 128/691

[58] Field of Search .................... 351/200, 205, 351/206, 213, 215, 246, 221; 354/62; 128/637, 691, 675

[56] References Cited

U.S. PATENT DOCUMENTS 5,016,643  5/1991  Applegate et al. .................... 351/221

*Primary Examiner*—Huy Mai
*Attorney, Agent, or Firm*—Pandiscio & Pandiscio

[57] ABSTRACT

An apparatus and method for comparing entoptically observed corpuscles with computer simulated images of corpuscle-like particles without requiring the observer to view more than one screen. Also disclosed are an apparatus and method for determining and documenting the size of the foveal avascular zone (FAZ). And an apparatus and method are disclosed for determining changes in the observer's leukocyte characteristics due to blue light flicker stimulation.

15 Claims, 24 Drawing Sheets

| | MODULE | FUNCTION |
|---|---|---|
| 1 | EVALUATION TEST, ALTERNATING | DISPLAY TWO SIMULATION FIELDS ALTERNATELY |
| 2 | EVALUATION TEST, SUPERIMPOSING | DISPLAY TWO SIMULATION FIELDS SIMULTANEOUSLY |
| 3 | EVALUATION TEST, SIDE-BY-SIDE | DISPLAY TWO SIMULATION FIELDS SIDE-BY-SIDE |
| 4 | BLUE FIELD TEST, ALTERNATING | DISPLAY SIMULATION FIELD & BLUE FIELD ALTERNATELY |
| 5 | BLUE FIELD TEST, SUPERIMPOSING | DISPLAY SIMULATION FIELD & BLUE FIELD SIMULTANEOUSLY |
| 6 | BLUE FIELD TEST, SIDE-BY-SIDE | DISPLAY SIMULATION FIELD & BLUE FIELD SIDE-BY-SIDE |
| 7 | FAZ SIMULATION | DISPLAY FAZ SIMULATION |
| 8 | PATIENT INFORMATION | INPUT/MODIFY PATIENT'S INFORMATION |
| 9 | REPORT | PREPARE THE TEST DATA & AGGREGATE RESULTS |
| 10 | SYSTEM CONFIGURATION | INPUT/MODIFY THE SYSTEM SETUP |
| 11 | HELP INFORMATION | PROVIDE HELP INFORMATION |

Fig. 16A

```
SUBJECT NAME: JOHN SMITH
SIMULATION-SIMULATION, SUPERIMPOSING:
17:32:02, 01/13/94
TRINUM  TM       REF.N TESTN N-AVE REF.V  TESTV  V-AVE  INIT.N INIT.V
   1,   17:33:08,   80,  79,   79,  20.00, 14.30, 14.30,   77,  11.80
   2,   17:34:13,   80,  76,   77,  20.00, 19.60, 16.95,    3,   9.60
   3,   17:35:07,   80,  83,   79,  20.00, 20.40, 18.10,   93,  10.40
   4,   17:35:48,   80,  79,   79,  20.00, 19.40, 18.42,   81,   8.40
   5,   17:36:35,   80,  82,   79,  20.00, 21.30, 19.00,  108,   0.80
SUMMARY
     AVERAGE NUMBER ± SD, PRECISION(%)
     79 ± 2.775 ( 3 PERCENT)

AVERAGE VELOCITY ± SD, PRECISION(%)
     19.00 ± 2.732 ( 14 PERCENT)

NORMALIZED NUMBER ± SD, ACCURACY(%)
     0.9870 ± 0.320 ( -1 PERCENT)

NORMALIZED VELOCITY ± SD, ACCURACY(%)
     0.95 ± 0.136  (-5 PERCENT)
                              REPORT PAGE 1
```

|   | FILE NAME | TYPE | FUNCTION |
|---|---|---|---|
| 1 | POSINIT.DAT | R | PROVIDE THE INITIAL POSITION OF SLS ON THEIR PATHS |
| 2 | FREF50.DAT | R | PROVIDE FULL SCREEN REFERENCE SLS PATHS, 50 PIXELS PER PATH |
| 3 | FTEST50.DAT | R | PROVIDE FULL SCREEN TEST SLS PATHS, 50 PIXELS PER PATH |
| 4 | HLEFT50.DAT | R | PROVIDE LEFT HALF SCREEN SLS PATHS, 50 PIXELS PER PATH |
| 5 | HRIGHT50.DAT | R | PROVIDE RIGHT HALF SCREEN SLS PATHS, 50 PIXELS PER PATH |
| 6 | SETTINGS.DAT | R/W | PROVIDE DEFAULT SYSTEM CONFIGURATION OR STORE CURRENT SETTING |
| 7 | OUTDATA.DAT | W | STORE ALL THE TEST RESULTS AND OTHER RELATED INFORMATION |
| 8 | REPORT.DAT | R/W | STORE/PROVIDE A REPORT FILE |
| 9 | BFINFO.TXT | R | STORE INDEXED TEXT FOR HELP INFORMATION |
| 10 | MODERN.FON | R | FONT FILE FOR GRAPHICAL TEXT |

Fig. 22

APPARATUS AND METHOD FOR DETERMINING CHARACTERISTICS OF A HUMAN RETINA USING ENTOPTICALLY OBSERVED LEUKOCYTES AND OTHER PSYCHOPHYSICAL PHENOMENONA

FIELD OF THE INVENTION

This invention relates generally to devices and methods used in ophthalmic diagnostic procedures, and more particularly to devices and methods of the sort that incorporate blue field entoptic phenomena.

BACKGROUND OF THE INVENTION

The blue field entoptic phenomenon is a visual perception of "flying" corpuscles in an observer's eye when that observer looks into a bright, deep-blue light. Ophthalmic diagnostic devices incorporating this phenomenon are well known in the art. Such devices have been used to diagnose various eye diseases such as amblyopia, diabetes, glaucoma, etc.

Furthermore, it has been reported that by observing the blue field through a rotating artificial pupil, an observer may perceive his or her own retinal vessels, including the foveal avascular zone (FAZ). This can be very useful, since the ability to accurately measure the size of the FAZ can provide a means for following the progression of some ocular diseases, e.g. diabetic retinopathy.

It has also been reported that causing the aforementioned bright, deep-blue light to flicker can induce changes in the blood flow characteristics of the retina.

One example of a prior art blue field diagnostic device is the Blue Field Simulator marketed by Oculix Inc. This device allows an observer to determine the number of corpuscles, their speed, and their pulsatility (i.e., their responsiveness to systolic and diastolic heart function) as the corpuscles pass through that observer's own retina.

The measurement technique utilized by the Oculix device consists of two steps.

First, the observer is asked to switch back and forth between two computer simulated screens displayed on the same computer monitor. The first screen is a reference screen displaying pre-determined corpuscle-like particles whose associated parameters are known only to the operator. The second screen is an adjustable screen, displaying adjustable corpuscle-like particles that the observer must adjust so as to match, from his or her own memory, the pre-determined corpuscle-like particles displayed on the first screen. By comparing these adjustment values, the operator can evaluate the reliability of the observer's responses.

Second, the observer is then asked to do the same operation, but this time comparing between a deep blue field (which causes the observer to perceive his or her own real corpuscles) and the aforementioned adjustable screen (which presents operator-adjustable corpuscle-like particles). The results are then evaluated, bearing in mind the reliability results obtained from the first step.

Unfortunately, the foregoing procedure is quite tedious and time consuming to perform. In addition, it is not suitable for every observer. For example, in some instances the reliability of the results obtained in the second step can not be deduced directly from the test results obtained in the first step. This is typically because the real corpuscles may differ significantly from the simulated corpuscles, and also because of the reliance placed upon the short term memory of the observer. In addition, because the simulated corpuscle-like particles displayed on the computer monitor of the Oculix machine have a lower contrast and brightness than the entoptically viewed real corpuscles, it can be difficult for observers having lower visual acuity (e.g., from diabetes or cataracts) to see the simulated particles.

In addition to the foregoing, the Oculix prior art device does not allow for either the determination of the size of the foveal avascular zone (FAZ) or the measuring of changes in the observer's blood flow characteristics due to blue light flicker stimulation.

OBJECTS OF THE INVENTION

One object of the present invention is to provide a novel ophthalmic diagnostic device which significantly increases the reliability of the results obtained when conducting blue field entoptic diagnostic procedures.

Another object of the present invention is to provide a novel ophthalmic diagnostic device adapted to compare entoptically observed corpuscles with computer simulated images of corpuscle-like particles without requiring the observer to view more than one screen.

Yet another object of the present invention is to provide a novel ophthalmic diagnostic device which does not rely upon the short term memory of the observer.

Another object of the present invention is to provide a novel ophthalmic diagnostic device which operates under the control of a personal computer.

Still another object of the present invention is to provide a novel ophthalmic diagnostic device which will yield reliable results with a broader range of patients.

A still further object of the present invention is to provide a novel ophthalmic diagnostic device which reduces the time required to make a reliable diagnosis.

Yet another object of the present invention is to provide a novel ophthalmic diagnostic device and method for determining the size and speed and pulsatility of leukocytes within the retinal capillaries of an observer.

Another object of the present invention is to provide a novel ophthalmic diagnostic device and method for determining and documenting the size of the foveal avascular zone (FAZ).

A further object of the present invention is to provide a novel ophthalmic diagnostic device and method for determining changes in the observer's leukocyte characteristics due to blue light flicker stimulation.

A still further object of the present invention is to provide a novel ophthalmic diagnostic device which is smaller in size than prior art devices.

Another object of the present invention is to provide a novel ophthalmic diagnostic device which is less expensive than prior art devices.

SUMMARY OF THE INVENTION

These and other objects of the present invention are achieved through the provision and use of a novel ophthalmic diagnostic device that is adapted for determining the number and speed and pulsatility of entoptically observed leukocytes in the retinal capillaries of an observer.

The device of the present invention comprises a display means for displaying a plurality of simulated leukocytes within the visual field of the observer so that the entoptically observed leukocytes are observed simultaneously with, and in the same visual field as, the simulated leukocytes. The display means comprise a first side and a second side, wherein the display means are adapted to transmit light from at least one of the sides thereof.

In the preferred embodiment, the display means are controlled by a programmable computer. A light source is disposed in spaced relation to the observer, and the display means is positioned between the light source and the observer, so that a first side of the display means faces the light source. A light diffuser is positioned between the light source and the display means. The light diffuser is adapted to scatter incident light from the light source so as to present a uniform illumination field to the display means. A lens is positioned between the light diffuser and the display means. The lens is adapted to collect light and to thereby provide a uniform background illumination to the display means. Filter means are disposed in front of the second side of the display means, between the display means and the observer. The filter means are adapted to restrict the wavelength of incident light that is emitted from the display means to a predetermined wavelength. Means for viewing the display means through the filter are also provided.

The preferred embodiment of the present invention operates as follows. A liquid crystal display (LCD) panel is interconnected to a personal computer (PC) so as to display images of corpuscle-like particles generated by the PC. The number and speed and pulsatility of these corpuscle-like particles may be adjusted at will by an observer. In operation, the observer will look at a blue light source through the LCD panel.

As a consequence of the blue field entoptic phenomenon, the observer will see their own corpuscles appear in their visual field. At the same time, the observer will also see the corpuscle-like particles generated by the personal computer and displayed on the LCD panel. Significantly, the simulated leukocytes generated by the computer and displayed on the display means will be viewed by the observer at the same time as, and in the same visual field as, the real leukocytes being viewed in the blue field. The observer will adjust the display parameters for the corpuscle-like particles until the corpuscle-like particles match the observer's own corpuscles in number, speed and pulsatility. Inasmuch as the present invention does not require the observer to switch back and forth between the blue field and the computer-generated display, and inasmuch as the present invention does not depend on the observer's visual memory, the present invention provides for an easier, faster, and more accurate method of conducting blue field entoptic diagnostic procedures.

In another embodiment of the present invention, the dimension of the observer's foveal avascular zone (FAZ) is determined by including a rotating artificial pupil between the blue light source and the observer. In this embodiment, the observer adjusts the size of a circle displayed on the LCD screen using computer controls so that the computer created circle matches the circular avascular region perceived from the observer's own retinal image.

In a further embodiment of the present invention, the blue light can be caused to flicker and thereby induce changes in the blood flow characteristics of the observer.

BRIEF DESCRIPTION OF THE DRAWINGS

These and other objects and features of the present invention will be more fully disclosed in, or rendered obvious by, the following detailed description of the invention, which is to be considered together with the accompanying drawings wherein like numbers refer to like elements and further wherein:

FIG. 16A is a list of the software's program modules and their function;

FIG. 22 is a list of data files used by the software of the present invention.

DETAILED DESCRIPTION OF THE INVENTION

Section 1. Introduction

1.1 Overview

Figure 1:
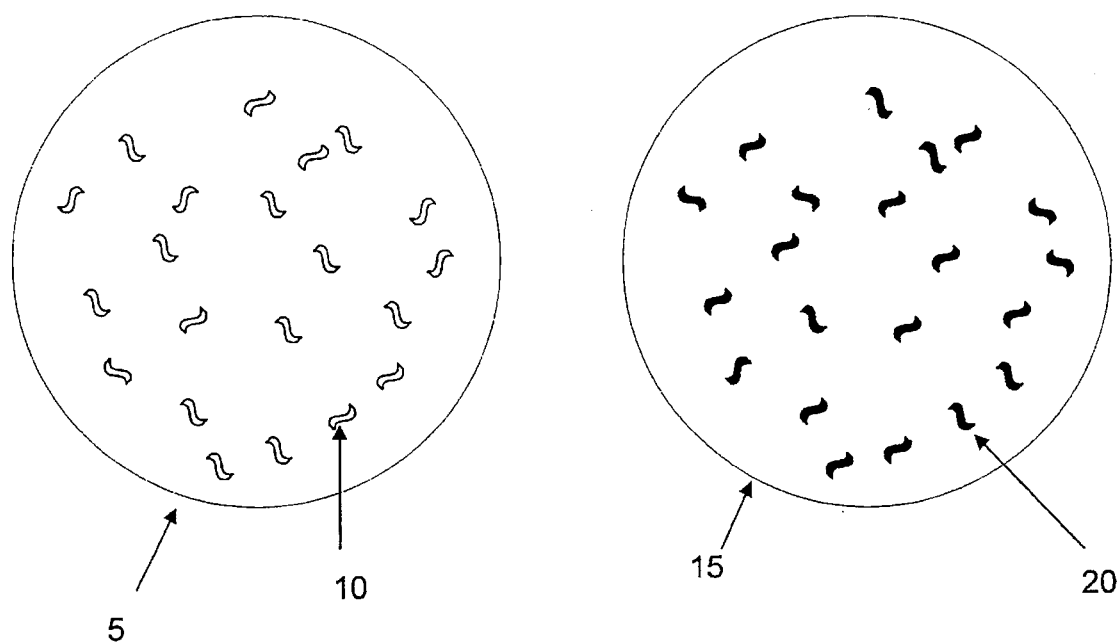
FIG. 1 illustrates the prior art alternating blue field simulation method.

When the image of a visual scene is projected on the fundus of the eye, it encounters a structure that is in reality part of the brain, i.e., the retina. It can be said that the retina represents the ultimate level of sophistication in the evolution of biological tissue. It has the ability to detect a few quanta of light and process a complex visual scene, transmitting the biological equivalent of up to half a billion bits of information per second.

The price of such performance is rapid energy consumption. The retina uses oxygen and glucose at a higher rate than other tissues in the body. Since these substances are supplied by both the retinal and choroidal circulations, the amount of blood flow in this area of the body, per unit time, per gram of tissue, is also very high. Therefore, the healthy function of the retina is dependent on the integrity of its blood supply and on a full complement of all the enzymes needed to keep the visual process operating at this rapid rate.

Determining retinal blood flow is fundamental to understanding the basic physiological process and pathological conditions of the visual system. Retinal blood flow is also used to evaluate the treatment &ocular diseases objectively. It has been suggested that some of the pathophysiology of diseases and disorders could be the partial occlusion of small capillaries so that blood cells cannot pass through them. The occlusion or rupture of the retinal capillaries, which may be caused by diabetic retinopathy, will cause the retina to die due to an inadequate blood supply. Other diseases such as hypertensive retinopathy constricts many of the small arterioles of the retina, resulting in retinal infarcts. In this respect it should be noted that the leading cause of blindness is retinal disease. This category accounts for 75% of all blindness.

Measurement techniques for quantifying retinal macular blood flow at the capillary level have been studied extensively. However, the current level of knowledge about the hemodynamics in those vessels is still very limited, because no adequate measurement technique has heretofore been developed.

The present invention teaches new psychophysical techniques and instruments for the study of retinal macular blood flow and the foveal avascular zone (FAZ) based on human entoptic phenomena. Psychophysics is one of the methods preferred by engineers and scientists, because it is non-invasive and because it allows measurements to be taken in vivo at the normal daily conditions of the tested patients or subjects. In addition, it may not require the assistance of highly trained medical personnel during medical examinations.

The present invention provides a new non-invasive technique for studying retinal macular blood flow and effecting FAZ measurement using human entoptic phenomena. Based on these measurement techniques, an innovative instrument using state-of-the-art electro-optical and computer simulation technology has been developed. The present invention also identifies some important characteristics necessary for better understanding and controlling the measurement process.

1.2 The Blue Field Entoptic Phenomenon

Entoptic phenomena are visual perceptions in one's own eye that can be visualized only under special stimulation conditions. The blue field entoptic phenomenon is a visual perception of leukocytes (also known as "flying" corpuscles) passing through the perifoveal retinal capillaries in an observer's eye when that observer looks at a homogenous, unpatterned, bright, deep-blue stimulation light. The best results can be obtained under the illumination of blue fight with a narrow wavelength band centered on 430 nm.

The physiological explanation of the blue field phenomenon is based on the nature of retinal blood flow and light transmission/absorption. As many as 60–70% of the photons passing through the retina in the pericapillary region will encounter one or more capillaries before reaching a photoreceptor. The capillaries of the retina are normally filled with red blood cells which move in single file. Occasionally, this motion is interrupted by a white blood cell or a plasma gap. Since the blue light is almost totally absorbed by the hemoglobin contained in the red blood cells, light reaches the photoreceptor only when it is not passing through red blood cells.

The leukocytes appear worm-like because of their elongation. In most microvascular networks, including those of the central retina, the capillary diameters are sufficiently small that the blood cells must deform to pass through them in single file. Leukocytes are temporarily trapped and take on a distorted elongated shape when they pass through retinal capillaries. This results from the small capillary diameter.

A leukocyte appears to have a luminous head and a dark tail when perceived in the blue field. Since the leukocytes temporarily decelerate flow in the capillary, a plasma gap with a lower hematocrit develops downstream and red blood cells which form a higher hematocrit accumulate upstream. The dark tail is presumably the upstream accumulation of red cells which greatly absorb the blue light. The luminous "worm" includes the plasma gap and the elongated body of the leukocyte, both of which are relatively transparent to the light.

Leukocytes visualized under the blue field phenomenon are characterized by three motion attributes: firstly, the movement proceeds recurrently along certain pathways defined by the capillary loops; secondly, the corpuscles are not seen in an area around the point of fixation known as the FAZ; and thirdly, the movement generally is not uniform, but rather is characterized by rhythmic accelerations which are synchronous with the cardiac pulse.

1.3 The Purkinje Phenomenon

A related blue field phenomenon, the Purkinje microvascular entoptic image, permits visualization of one's own perifoveal capillaries. This phenomenon is caused by viewing a homogenous blue light source through a pinhole. This phenomenon occurs when the periodic motion of the pinhole is within a range smaller than the observer's pupil. If fixation is completely steady, all objects in the visual field would gradually disappear due to retinal fatigue. The planetary motion of the pinhole changes the light beam entry location within the pupil, which then varies the angle at which the light hits the retina. Since the vascular shadows cast at the photoreceptors are constantly moving, this allows one to entoptically visualize the retinal vessels.

The surface area and thickness of the retina are typically about 17 $cm^2$ and 0.2 mm, respectively. The retina is actually an exposed part of the central nervous system showing a highly differentiated structure. The central area of the retina which lies in the optic axis of the eye is essentially avascular. In this area, the innermost retinal layers and the rods are absent. This area, known as the foveal avascular zone (or FAZ), is the area of highest visual acuity and contains 9,000 to 13,000 cones. The FAZ can be perceived using the Purkinje phenomenon, i.e., the FAZ is the circular area at the center of the retinal vascular image where no capillaries exist. The dimension of the FAZ is known to be very informative in the diagnosis of certain retinal diseases.

1.4 Current Retinal Blood Flow Measurement

As early as 1860, it was suggested that the speed of leukocytes perceived under the blue field phenomenon could be used to determine the retinal blood flow. In capillaries which have a diameter of between about 7 and 10 μm, the speed of leukocytes is equal to the mean speed of the whole flow. Changes in leukocyte velocity would reflect changes in blood flow if the capillary diameter can be assumed to remain constant during the test. The constancy of the diameter of the retinal capillary has been supported by several studies.

Over the years, many attempts were made to measure the speed and number of leukocytes based on the blue field phenomenon. However, none of the techniques utilized became a routine clinical tool in retinal circulation examinations because there was no objective means to quantify the leukocyte motion. In the early 1980's, a computer simulation method was developed to indirectly determine the characteristic of the leukocytes. This method consists of having subjects compare and match the characteristics of their own leukocytes (perceived under the blue field phenomenon) with simulated leukocytes produced by a computer. With this measurement technique, subjects are first asked to view their retinal leukocytes under the stimulation of bright, uniform blue light. Then the subjects are required to switch to a computer screen displaying simulated leukocytes (SLs) whose number and velocity are adjustable. Subjects are instructed to match the parameters of their real leukocytes (seen entoptically) with the SLs created by the computer by adjusting the parameters of the SLs using computer controls. Thus it will be seen that by using this technique, the parameters of real leukocytes can be measured indirectly by SLs. An instrument based on this technique, the Blue Field Simulator (BFS-1000) from Oculix, Inc. allows for the investigation of retinal blood flow, as well as the diagnosis of clinical eye disease such as amblyopia, glaucoma, etc.

The matching process discussed above requires the subject to swap between the blue field and the computer simulation screen a number of times. The blue field view and the simulation screen view are very different in patterns and in the intensity of illumination. The intensity of illumination that a computer monitor provides is far less than the intensity of illumination from the entoptoscope. Since there is a strong illumination contrast between the two fields, testing can be tedious and tiring and is not always applicable to every patient. Furthermore, the Oculix instrument includes a built-in microcomputer and other special hardware for interfacing the computer and entoptoscope and, as a consequence, it is relatively bulky and costly.

1.5 Current FAZ Measurement

A reliable technique for evaluating retinal vascular structure (including FAZ measurement) is essential in the diagnosis and monitoring of retinal vascular disease. However, the spatial distribution of the vascular network of primate retinas, including humans, has been the subject of surprisingly little quantitative study.

Currently, the most widely used technique to study retinal vascular structure is fluorescein angiography. This technique is based on the property of the fluorescein molecule to demonstrate fluorescence. When injected into the blood circulation, 60% of sodium fluorescein is bound to plasma proteins, particularly to albumin. Although fluorescein angiography is by far the most widely used method to display fluorescence in the ocular fundus, the intravenous injection of fluorescein can cause side effects and complications such as nausea, vomiting, cold sweats, dizziness, fainting, local skin irritation and thrombophlebitis. In addition, the fluorescein angiography can only provide a detailed view of the retinal vessels when the ocular media are clear.

Studies have also been conducted with respect to the psychophysical evaluation of retinal vessels and FAZ measurement. These techniques are based on the Purkinje phenomenon, which allows one to visualize their own retinal vessels. The most recent work was conducted by using computer simulation technology. Subjects are asked to compare their entoptical visualization of retinal vessels and FAZ with the computer simulated screen. To measure the size of FAZ, subjects need to switch between two fields and adjust the size of the simulated FAZ. With this technique, subjects need to use their temporary memorization to recall the image that they entoptically perceived while they are adjusting the simulated one. This constant switching and matching process is difficult to perform and less reliable results may be expected.

Section 2. The Blue Field Simulation Technique of the Present Invention 2.1 Overview The fundamental principle of blue field entoptic simulation is to measure the attributes of retinal leukocytes by matching those attributes with the attributes of leukocytes simulated by a computer. This matching can be done by adjusting the number and velocity and pulsatility parameters of the simulated leukocytes (SLs) until they appear close to the ones perceived in the blue field.

2.2 Method of the Comparison Procedure

There are two ways for a human to examine and compare two different scenes: alternating or superimposing. The alternating method involves looking at one scene at a time and making a comparison using the observer's short term visual memory. The superimposing method involves simultaneously displaying two different scenes on a single display field.

In the prior art, the alternating comparison method is used. The adjustable field where the parameters of the simulated leukocytes can be easily varied is defined as the test field. The non-adjustable field being matched is defined as the reference field. FIG. 1 illustrates the pattern of an alternating method. The observer can only view one field at a time. The field 5 where leukocytes 10 have white tails is the reference field, and the field 15 where leukocytes 20 have black tails is the test field. The matching process involves examining the reference field, memorizing the perceived leukocyte's motion characteristics, switching to the test field and then adjusting the parameters of the test field leukocytes accordingly. There is no limitation for how many times the swapping of the fields can be performed. This is the only method that is currently being used in the prior art for the application of blue field simulation.

Figure 2:
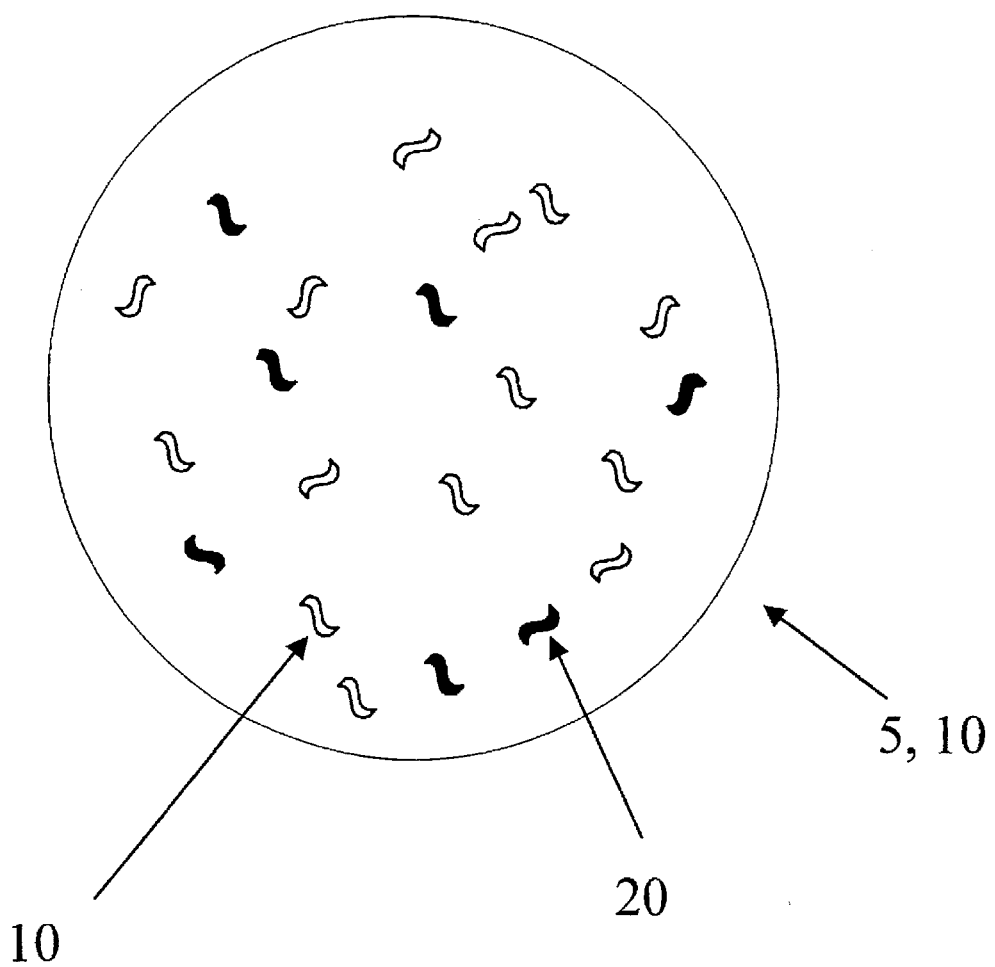
FIG. 2 illustrates the superimposing blue field simulation method of the present invention.

FIG. 2 shows the new technique of superimposing the two fields simultaneously against one another. The white leukocytes 10 belong to the reference field and the black leukocytes 20 are from the test field. Both fields can be observed at the same time. As a result, matching can be done without swapping back and forth between the two fields, and without the need to temporarily memorize the reference field.

In an alternative arrangement, a side-by-side implementation can be used to compare the two fields. More particularly, this technique vertically divides one screen into two parts, with each field being represented by one part.

Figure 3:
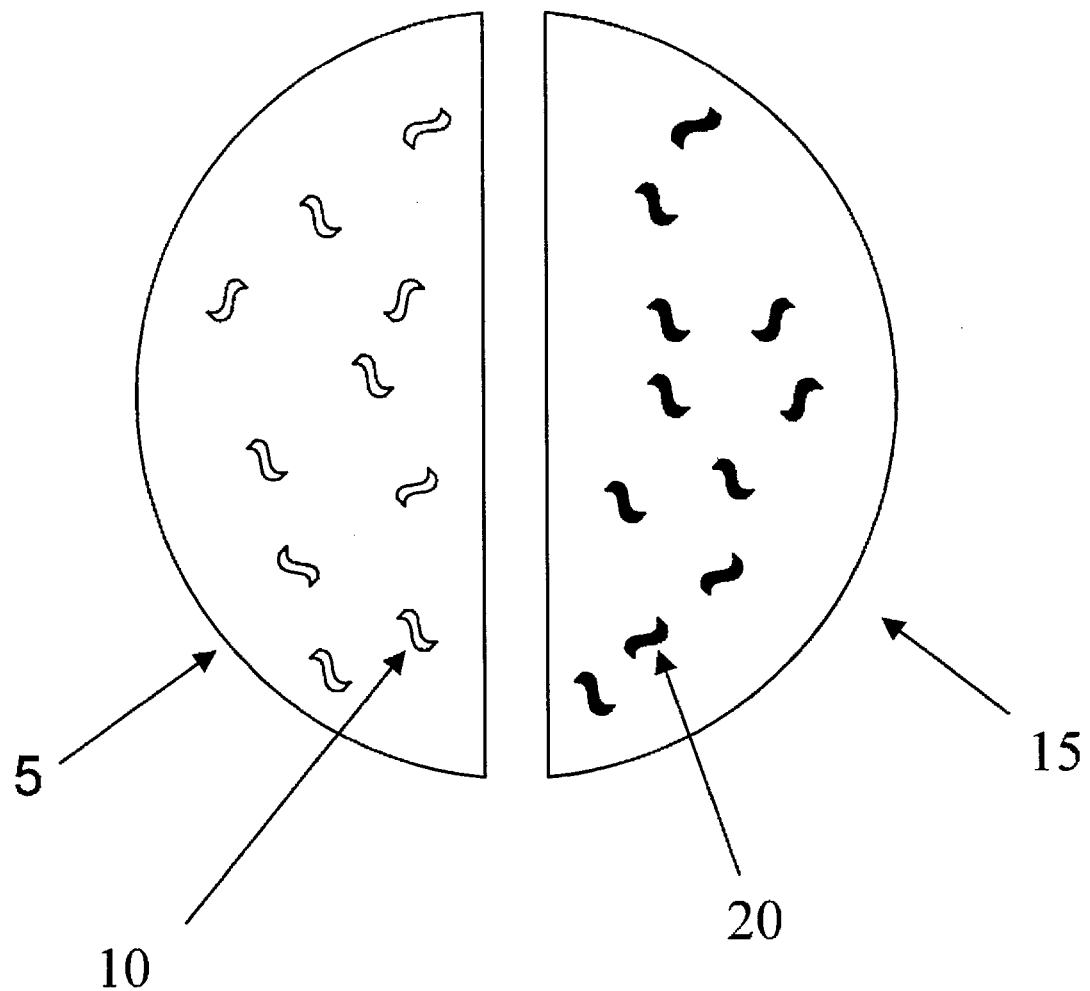
FIG. 3 illustrates the side-by-side blue field simulation.

FIG. 3 is an illustration of this side-by-side technique. The reference field 5 (with its leukocytes 10) and the test field 15 (with its simulated leukocytes 20) are displayed on the same screen simultaneously. The two fields are separated by a vertical gap. For blue field simulation, the side-by-side technique can be understood as only half of the retina being exposed to blue field stimulation. The other half of the retina has a regular viewing of the computer simulation. Therefore, an assumption that leukocytes have a uniformed distribution on the retina must be made.

It should also be appreciated that, within the context of this document, the term "side-by-side" is meant to include any split combination of two separate images into a single view, i.e., it includes the side-by-side arrangement of FIG. 3, a split top-and-bottom arrangement, etc.

Section 3. The Blue Field Simulation Hardware System of the Present Invention

3.1 Introduction

The present invention comprises two functional parts, the blue field stimulator and the apparatus for visualization of microvasculature entoptic image (AVMEI). A novel feature of the present invention is the utilization of a 2-D Spatial Light Modulator (SLM) to generate SLs and simulated FAZ images superimposed on blue light. The use of a 2-D Spatial Light Modulator (SLM) provides for the integration of features such as alternating, superimposing, and side-by-side comparisons in the blue field simulation methods, as well as FAZ evaluations, in one single compact instrument. The present invention can be controlled by a general purpose personal computer (PC) (and associated software such as that shown in the attached Appendix A) without the need for special interface hardware. The adaptation of a state-of-the-art, real-time SLM provides for a highly compact, inexpensive and comprehensive device.

The optical system of the present invention generally comprises a light source, diffuser and collection optics, a 2-D spacial light modulator, a filter and an eyepiece. The detector of the system is the human eye.

3.2 SLM Evaluation and Selection

The SLM is one of the most critical components in optical information processing systems. The SLMs available today can be categorized into five areas: liquid crystal devices (LCDs), deformable mirror devices (DMDs), magneto-optical devices (MODs), electro-optic devices (EODs), and acousto-optic devices (AODs). Of these modulators, only AODs have found widespread use outside the laboratory. Most of these SLMs suffer from either low resolution, low speed or low optical efficiency. Each of these SLMs has one characteristic in common—they are relatively expensive. Recently, however, an addition to the SLM market, liquid crystal television (LCTV), has offered many of the same or even better characteristics with a significant decrease in cost. The rapid evolution of the LCD technology, however, has made the LCTV appear to be the most suitable SLM for use with the present invention.

High resolution, high contrast ratio, high speed, small size, ease of interface and low cost are significant criteria for the selection of the SLM to be used in connection with the present invention. In particular, the resolution should be sufficient to display at least 200 SLs, where each SL has a length of at least 6 minutes of arc. A contrast ratio of greater than 20:1 is often necessary. The speed must be fast enough to keep pace with the average screen update rate (50 ms) controlled by the simulation software of the present invention. The size of the SLM should be 2"–9" (as measured diagonally across the device). The SLM pixel structure must be suitable to generate a uniform field. The computer interface should preferably be compatible with EGA/VGA devices, although compatibility with NTSC, PAL and SECAM is also acceptable. The cost should be acceptable for a home care user, i.e., less than about $500.

Various LCTV's have been identified for use with the present invention.

For example, one SLM that is suitable for use with the present invention is the Sharp TFT LCD Video/Computer Projector (XG-800U). The 3.6" LCD delivers a video image with up to 560 lines of horizontal resolution, and is fully VGA compatible with 640 by 480 resolution. The built-in control circuit allows the VGA image to be directly converted to LCD panels. Elimination of a D/A signal conversion allows for a sharper image to be obtained. Furthermore, at a visual field of 15°, there are no pixel structure problems with the Sharp system. The Sharp system's contrast ratio is reported to be 100:1.

Another SLM that is suitable for use with the present invention is the Proxima Ovation 810, a color TFT AMLCD computer projection panel. It is equipped with an 8.4" color AMLCD panel that has a resolution of 640 by 480. Each pixel has a dimension of 0.27 mm by 0.27 mm. The drive circuit is fully compatible with EGA/VGA and no hardware interface is required. The adjustable contrast ratio can be up to 200:1.

Both the Proxima Ovation 810 and Sharp XG-800U have similar optical quality and computer interfaces. The Proxima Ovation 810 can be considered as a larger version of the LCD panel used in the Sharp XG-800U. In a preferred embodiment of the present invention, the Proxima Ovation 810 is used as the SLM device. Due to the large size of the LCD panel, other optical components used in the present invention need to be enlarged accordingly.

3.3 The Design of the Blue Field Entoptoscope

The entoptoscope of the present invention is designed to deliver a Maxwellian illumination to the ocular fundus at a wavelength of 430 nm and an intensity of approximately 15 cd/m$^2$. The diameter of the illuminated field is approximately 12 degrees.

Figure 4:
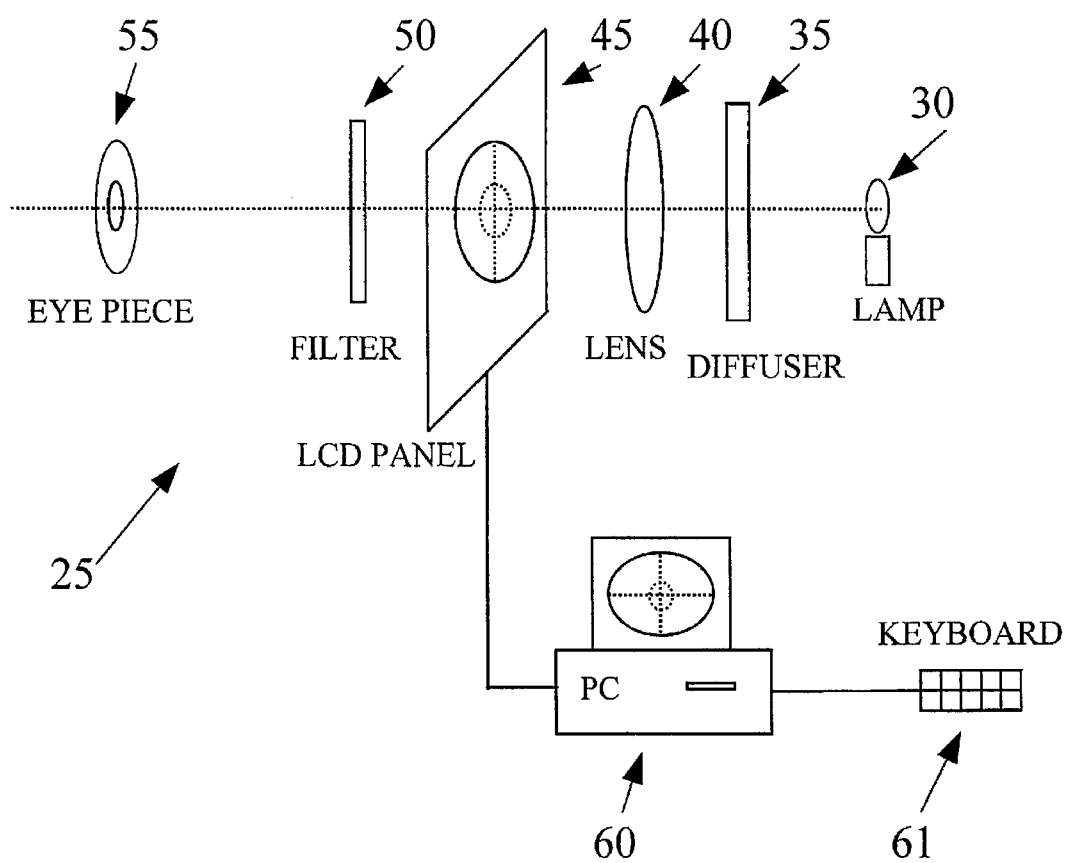
FIG. 4 is a schematic view of one embodiment of the optical setup of the present invention.

One preferred embodiment of the present invention is shown in FIG. 4. The entoptoscope 25 generally comprises a light source 30, a diffuser 35, a lens 40, an SLM 45, a filter 50 and an eyepiece 55.

More particularly, the light source 30 comprises a 360W projection lamp (ENX Apollo, 82 V). The lamp is powered by 110 V AC (60 Hz) through a transformer. The intensity of the light is adjusted by the effective voltage applied to the lamp. As a default setting, the illumination at the eyepiece is measured as 96 cd/m$^2$ without a blue filter.

Heat dispersion is an issue since both the lens and the filter have a limited capacity for withstanding heat. In the present invention, part of the heat is absorbed by diffuser 35, which is located between lens 40 and lamp 30. An electric fan (not shown) may be installed to generate an air flow through vents. The level of heat at the eyepiece 55 is considerably lower because narrow band blue filter 50 also absorbs heat.

It has been found that the structure of the reflector and the filament of the projection lamp 30 may cause a poor uniformity of illumination. The function of diffuser 35 is to scatter incident light from the light source so that a uniform illumination field may be provided. The diffuser of the present invention should, preferably, approximately follow Lambert's Cosine Distribution Law so that there is a significant "loss" of collimated beams. The thermal property of the diffuser is also a critical aspect, since it is positioned only about 10 mm away from lamp 30. There is no special spectral range requirement for diffuser 35, as long as the bandwidth around 430 nm is included. In one preferred embodiment of the invention, a thin layer of opal diffusing glass from a SYLVANIA Flood Reflector lamp was used to form diffuser 35. The optical and thermal properties of this material make it suitable to serve as a diffuser for the present invention. Advantageously, the diffuser absorbs heat from the lamp which reduces the heat impact on the lens.

The function of lens 40 is to collect the light and to provide a uniform background illumination. Since the SLM has an effective display area of 171 mm by 130 mm, a Fresnel lens with overall size of 433 mm by 433 mm is preferred. The focal length of the lens is around 177 mm. A preferred Fresnel lens comprises a flat, thin piece of acetate butyrate in which a series of small concentric stepped zones are molded. They extend from the center to the outer margins. These lines are about 0.2 mm wide. Each concentric line acts as part of the lens. Collectively, the concentric lines form the function of a true lens. The lens transmittance is greatly increased over that of other, conventional lens of the same focal length. One of the drawbacks of a Fresnel lens is that the lines pattern may be viewed if no other optical components are used to improve the image. In the present invention, however, each line on the lens has a visual angle about 1.37 minutes of arc. This is small enough to effect the desired perception of blue field phenomenon.

It has been reported that leukocytes can be optimally perceived with an entoptoscope that provides uniform illumination of the retina at a wavelength $\lambda$ of 430 nm. In the present invention, an interference filter 50 with a central wavelength of 430 nm is preferred, such as that sold by Oriel Co., #59295, $\phi$=50.8 mm. This interference filter has a peak transmission greater than 40%. The bandwidth at 50% of its peak transmittance is 9 nm. Due to its narrow bandwidth, the filter blocks as much as 85% of the light intensity.

3.4 The Design of AVMEI

Still looking now at FIG. 4, it will be seen that the blue field entoptoscope 25 also includes the LCD 45 described above, and the PC 60 (including user input keyboard 61) used to form the simulated leukocytes on LCD 45 as will hereinafter be described in further detail.

In an alternative embodiment of the present invention, the Purkinje phenomenon is used for FAZ analysis. More particularly, the Purkinje phenomenon can be realized by viewing a blue luminated background through a pinhole that follows a periodic motion. The motion of the pinhole may be circular or linear. This periodic motion constantly changes the beam entry location within the eye's pupil and varies the angle at which the light strikes the retina. Compared to the blue field phenomenon, the Purkinje phenomenon does not require a narrow bandwidth of blue light.

This alternative embodiment of the invention may comprise either linear or circular motion pinhole arrangements.

3.4.1 The Linear Motion AVMEI

Figure 5:
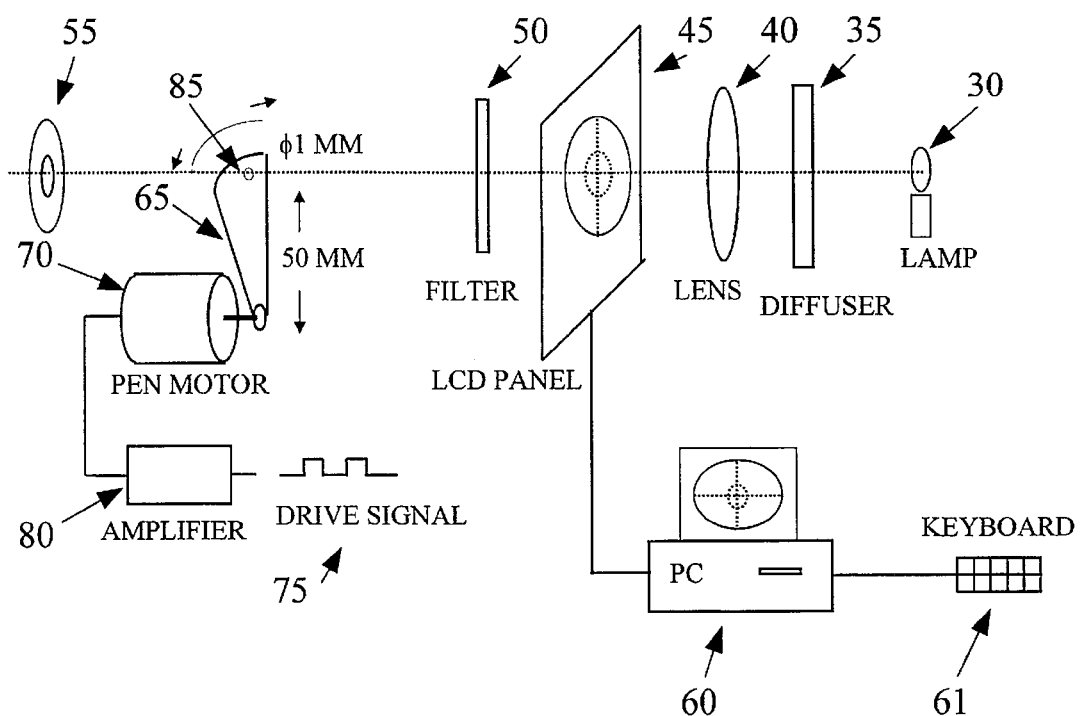
FIG. 5 is a schematic view of the linear AVMEI of the present invention.

In a linear vibration motion pinhole assembly, a piece of black plastic sheet 65, a galvanometer 70 (Pen motor, MYE, model RS-077), a square wave generator 75 and an amplifier 80 to drive the motor may be assembled in the manner shown in FIG. 5.

Black plastic sheet 65 comprises a triangular shape. The smaller end is secured to the shaft of the motor 70. The larger end includes a hole 85 of 1 mm diameter. The distance between the hole and the shaft is 50 mm. The motor 70 is driven by an amplifier 80 and controlled by a square wave generator 75 which has an adjustable frequency and amplitude. Accordingly, the pinhole can be moved about with an adjustable frequency and displacement.

The uniform blue illumination is generated as disclosed hereinabove. Since the pin hole allows a very small amount of light to be transmitted through to the eye, the luminous flux of the blue light is very limited.

In order to elicit the Purkinje phenomenon, the observer's eye needs to be located very close to the pin hole. The muscle of the eye ball should be completely relaxed as if one is looking an infinite distance. The vibration frequency range is about 1 Hz to 10 Hz and the amplitudes range of the vibration is about 5 mm to 15 mm. The frequency and amplitudes need to be adjusted until the retinal capillary net and the FAZ are clearly visualized. The direction of the motion of the pin hole does not effect the visualization of the retinal capillary net and the FAZ.

3.4.2 The Circular Motion AVMEI

Figure 6:
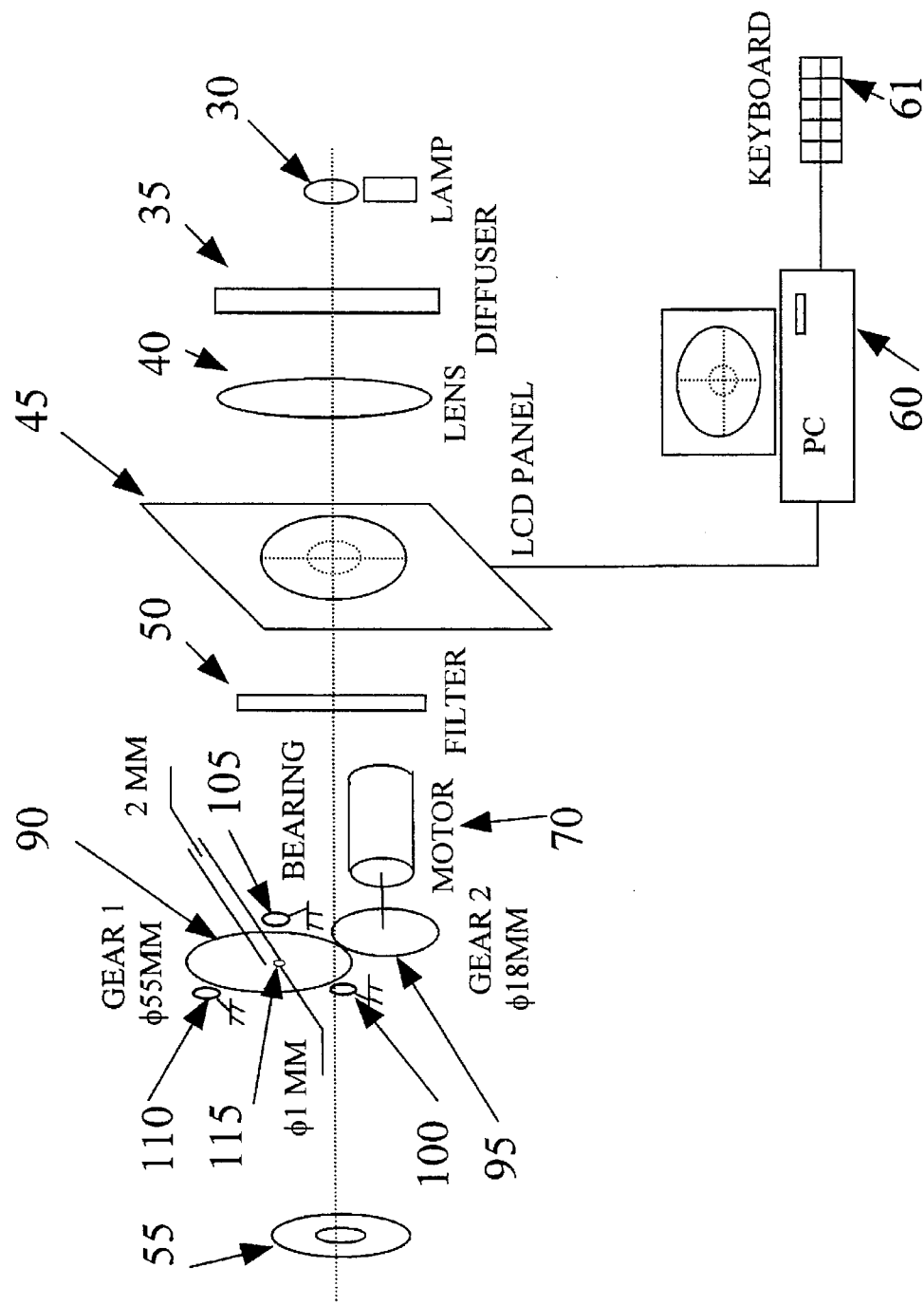
FIG. 6 is a schematic view of the circular AVMEI of the present invention.

Apparatus for creating circular pin hole motion is shown in FIG. 6. This embodiment comprises a DC motor 85, 2 gears 90 and 95, and 3 bearings 100, 105 and 110.

Gear 90 ($\phi$18 mm) is driven by the DC motor 70. The rotating speed is controlled by the DC power supply (HP6291A). Gear 95 ($\phi$55 mm) is secured by three bearings 100, 105 and 110 ($\phi$4 mm) and driven by gear 90. There is a 1 mm diameter hole 115 located 2 mm off center of gear 95. When gear 95 is rotated, the pin hole will rotate at a 4 mm diameter circular trace. The blue light is provided by the blue field entoptoscope 25 of the present invention as disclosed hereinabove.

To view the Purkinje phenomenon, one should place the eye close to gear 95 and look at the center with the ocular muscle relaxed. As the pin hole rotates, one is able to see the blue light through the pin hole. Within a rotating speed of around 1.5–9 revolutions per second, one's perifoveal capillaries can be perceived. Usually, there is an optimal rotating speed that causes best perception for each individual. The optimal speed may vary among individuals.

3.5 Speed and Displacement Conversion

With the device of the present invention, in order to estimate the velocity of leukocytes and the size of the FAZ, a conversion needs to be performed between the dimension of an object on the SLM 45 and its projection on the observer's retina. The actual image size of a projection from SLM 45 to the observer's retina is derived from the optical geometry illustrated in FIG. 7. The image size on the retina is a function of the object size on the SLM, the object distance between the SLM and the eye, and the image distance of the eye.

Figure 7:
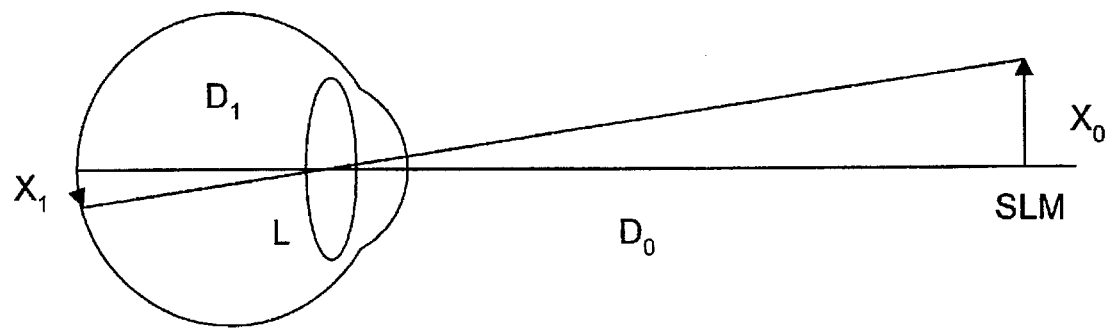
FIG. 7 is a diagram showing the relationship between the actual image size of a projection from the SLM of the present invention and the optical geometry of a human eye.

In FIG. 7, $D_0$ is approximately the distance between the SLM and the eye. $X_0$ represents the height of an object on the SLM. L is the eye's lens. In a human eye, the image distance $D_1$ from the eye lens to the retina is constant. Therefore, the image size of $X_1$ can be obtained through the following equation:

$$X_1 = (D_1/D_0)X_0 \tag{3.1}$$

Since the present invention offers real-time simulation, the relationship between the velocity of an object on the SLM and the velocity of its image on the retina can be derived from equation 3.1.

$$V_1(t)=(D_1/D_0)V_0(t) \qquad (3.2)$$

where, $V_0(t)$ represents the object's velocity on the SLM and $V_1(t)$ represents its image velocity on the retina.

In the present invention, the distance between the SLM and eyepiece ($D_0$) is fixed at about 470 mm. $D_1$ is assigned a value of the typical anteroposterior diameter of the eye, i.e., 25 mm which is the average distance between the lens and retina for human eyes.

All the conversions are calculated by the software used by the system.

As a result of choosing an LCD as SLM, the present invention comprises both alternating and superimposing blue field simulation methods as well as FAZ simulation. This has proven to have the advantages of being economical, compact, flexible, easy to use and efficient. It makes it possible for users to connect the device of the present invention to their office or home PCs and requires no further additional equipment.

Section 4. The Blue Field Simulation Software System

4.1 Introduction

The operation of the Blue Field Simulation System (BFSS) is controlled by an IBM PC (PC) or another appropriate computer. More particularly, the blue field simulation, FAZ simulation, the computer user interface, data storage and data analysis are all manipulated by the software system of the present invention. The software system of the present invention is designed to be self-contained and user friendly. The simulation software includes the prior art technique of an alternating comparison under the blue field phenomenon, as well as the present invention's novel superimposing comparison technique. The software also permits sided-by-side comparisons to be made under the blue field phenomenon. The simulation software also includes FAZ simulation. In a preferred embodiment, two operation modes are provided, a simulation to simulation comparison for identifying the reliability of the subject's responses, and a simulation to blue field comparison for actual subject diagnosis. Preferably, all function modules are integrated by an interactive graphical user interface (GUI).

The computer program of the present invention was written in Microsoft C/C++ (Version 7.0) and Microsoft assembly language using object oriented programming techniques. There are approximately two thousand lines of source code and twenty five thousand bytes of executable program in the software. The system software is set forth in the enclosed Appendix A. The system can be directly installed on a PC or its compatible which is equipped with an EGA/VGA graphics card.

4.2 Design Concept

The software of the present invention is designed so as to have high speed, be self-contained and be user friendly. The software program is preferably loaded in a general purpose PC. The software interfaces with the hardware of the present invention through an EGA/VGA card, without any additional hardware accessory being required. The high speed, real-time simulation must be achieved solely by the maximum utilization of the EGA/VGA graphics adapter. The graphic routines and simulation algorithms are specially developed by directly accessing the display memory and the graphics registers on the adapter. The screen flicker effects, screen clear timing, the interval between two frames, and the speed of floating point calculations need to be carefully considered.

The software of the present invention is designed to utilize object oriented programming techniques. The software system is a relatively complex system, containing eleven different interdependent modules including all alternating, superimposing, and side-by-side blue field simulation methods, and the FAZ simulation. These modules have their own independent functionality and also need to be linked with other modules. The object oriented programming approach provides an efficient way to implement the source code and, equally importantly, makes program maintenance easier.

The user friendly interface is another important factor for such a complex software system. The GUI environment allows a user who has limited knowledge of the program to operate the present invention without additional help. A graphical, menu-driven structure and an on-line help feature are also included in the program.

4.3 EGA/VGA Adapter and Graphics Modes

A graphics adapter interfaces a computer to a video monitor. There are several standard graphics adapters available for use with PCs. The software of the present invention is programmed to run on an Enhanced Graphics Adapter/ Video Graphics Array (EGA/VGA) adapter which is widely used by IBM-compatible PCs. The EGA/VGA adapter contains control registers, display memory, interface circuits and video output circuitry. It can be configured into one of several alphanumeric or graphics operation modes.

In the present invention, an EGA/VGA adapter is employed to drive both the computer monitor and the SLM (LCD panel). The system software interacts with the EGA/VGA in two ways; the first is through the control registers, and the second is through the display memory. The control registers are assigned I/O port addresses, whereas the display memory is mapped into the host memory address space.

4.3.1 Display Memory

Computer graphics is memory intensive. A single image of blue field simulation occupies over 112 KBytes of memory. In the EGA/VGA adapter of the present invention, the display memory is mapped directly into the PC's memory address space and organized in a straightforward manner. The memory is segmented into bit planes. A bit plane contains one bit for each pixel. It can occupy a maximum area of 128 KBytes from A0000 hex to BFFFF hex in the host memory space per plane. The display memory interfaces to the host processor through an 8-bit data bus. The display memory can be organized into a variety of resolutions depending on the display mode, i.e. several low-resolution pages or one high-resolution page.

A byte (8 bits) can be written to the display memory when the EGA/VGA adapter is in the graphics mode. A program can write a byte into the display memory by directly accessing the display memory or by using the computer's BIOS calls. Using the BIOS calls is simpler but much slower. Since the blue field simulation of the present invention requires rapid full-screen updates, the graphics routines provided by the C compiler library (which primarily use the BIOS calls) are not fast enough; consequently, a flickering might occur. Furthermore, it is easier to convert a program with direct memory access graphics routines to other computer platforms or a single chip computer.

The EGA/VGA display memory is constructed from dynamic read/write memory (RAM). It uses the top left corner of the display as the lowest display memory address. In the present invention, the display memory is thought of as one-dimensional. The total number of bytes required for a screen on each bit plane is obtained as follows:

$$\text{Number of bytes} = \frac{\text{Number of columns}}{8} \times \text{Number of rows} \quad (4.1)$$

Figure 8:
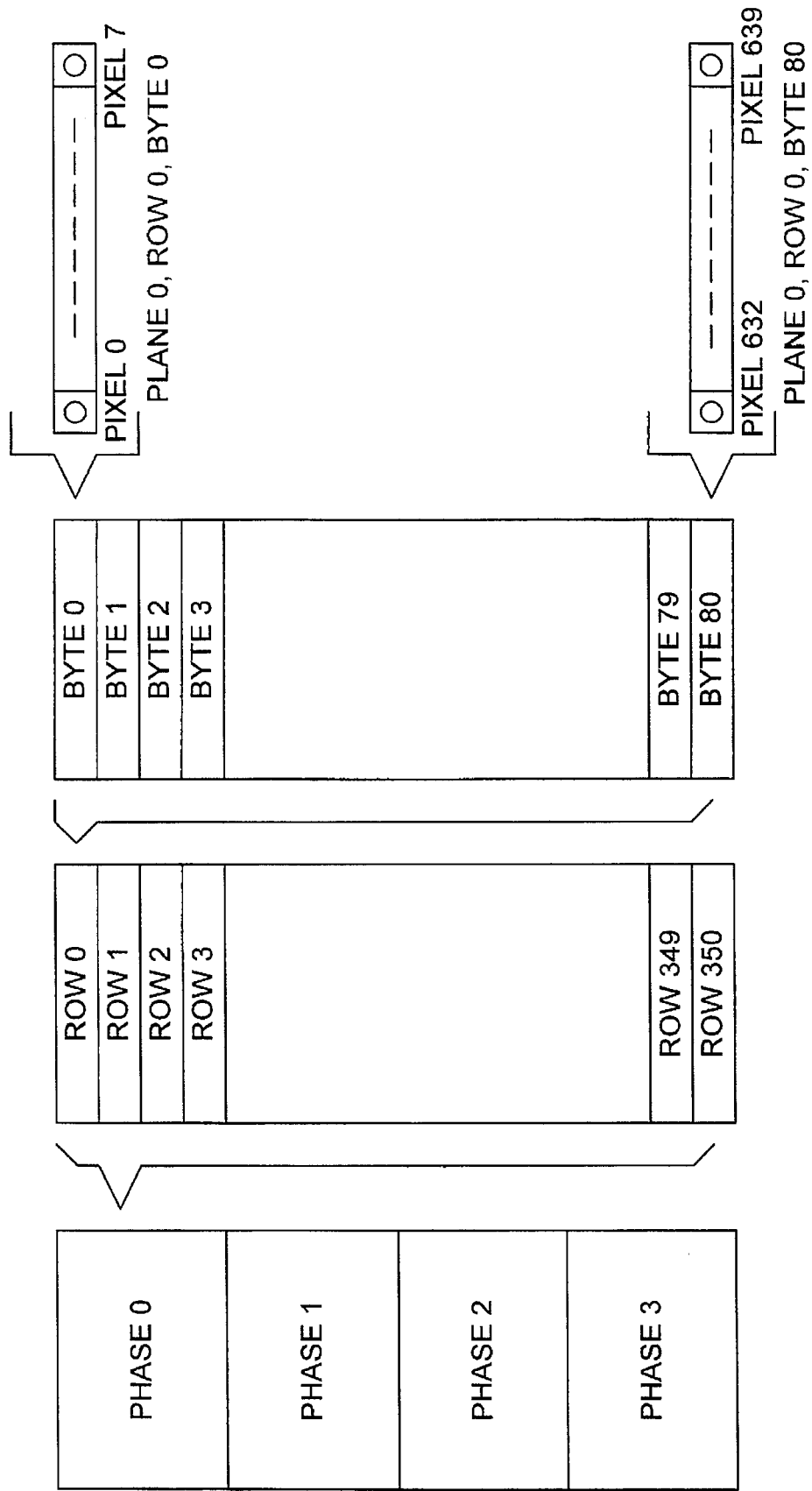
FIG. 8 is a diagrammatic illustration of the VGA display memory bit planes.
Figure 9:
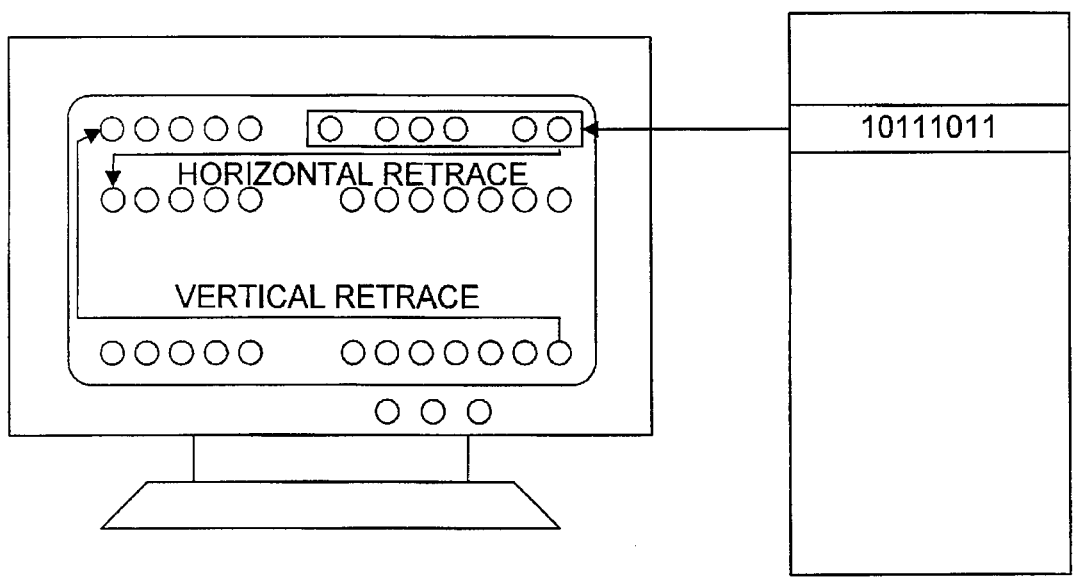
FIG. 9 is a diagrammatic illustration of the mapping of a byte in display memory to the monitor.

Typical EGA/VGA implementations include four 64 KBytes bit planes for a total of 256 KBytes of memory. The organization of the VGA's display memory bit plane is shown in FIG. 8. The data in the display memory is output to the monitor through the video hardware section on the EGA/VGA adapter. A byte in display memory is translated onto the monitor as eight neighboring horizontal pixels, as shown in FIG. 9. The host can read or write to display memory without having to wait for the horizontal or vertical retrace periods.

Figure 10:
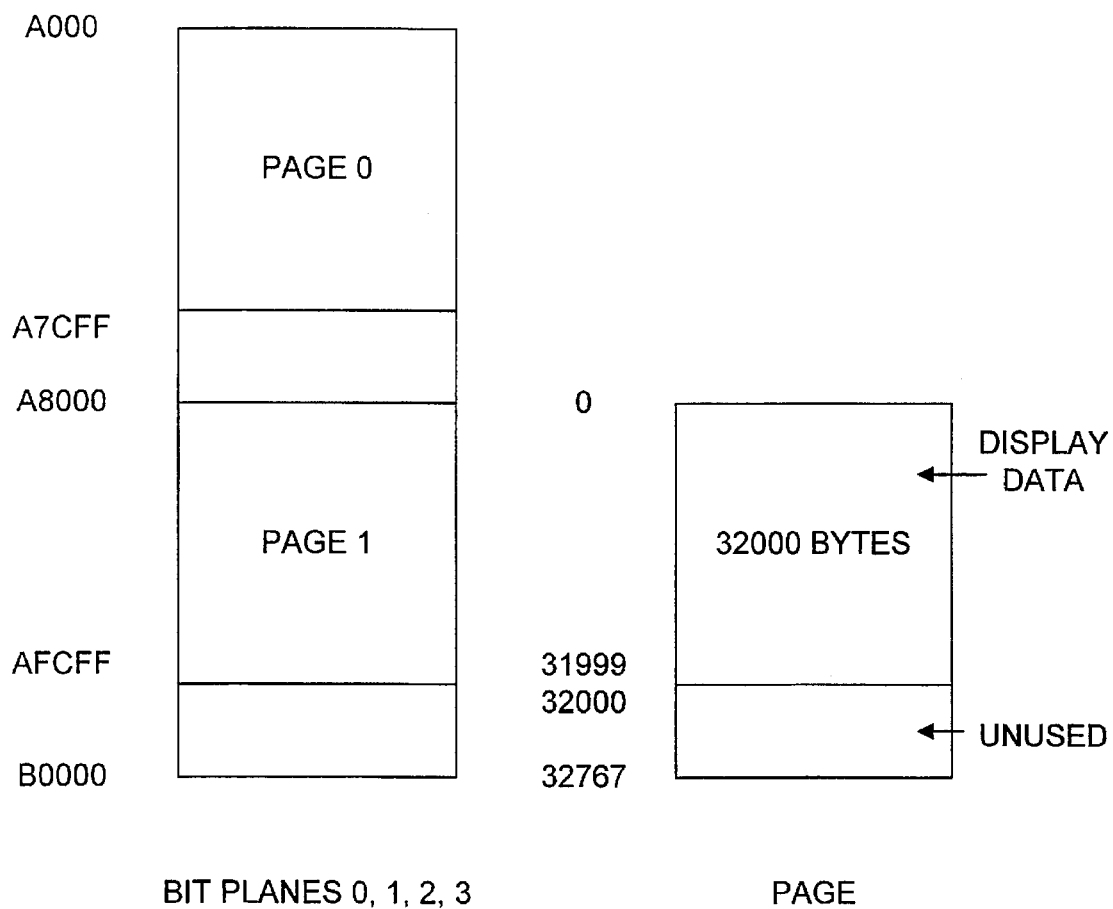
FIG. 10 is a diagrammatic illustration of the EGA/VGA Mode 10 display memory map used in connection with the present invention.

In the present invention, the EGA/VGA card is programmed in Mode 10 which uses a display resolution of 640 horizontal pixels per scan line and 350 scan lines. This is equivalent to 224K pixels. There are 64 KBytes per plane and the starting address is A0000 hex. For the double buffering animation technique, two pages are divided between the addresses of A0000 hex and B0000 hex on each plane. Eight pixels compose a byte, so there is a total of 28 KBytes per page on a bit plane. FIG. 10 illustrates the display memory map for EGA/VGA Mode 10 hex.

4.3.2 Resolution

Two issues of significant importance in computer graphics are the amount of spatial resolution and the color resolution.

The EGA/VGA adapter provides a high-resolution mode of 640 by 480 pixels, but the spatial resolving power of the human eye at normal screen viewing distances goes far beyond the 640 by 480 resolution. However, the tradeoffs involved in adding resolution are cost, processing time and storage requirement. In the software of the present invention, EGA/VGA graphics Mode 10 (hex) (640 by 350) is used for the blue field simulation, which requires high speed performance. GUI screens utilize graphics Mode 12 (hex) (640 by 480), since the speed obtained is sufficient for the user interface.

The color resolution includes the total number of possible colors and the number of colors that can be displayed simultaneously. The EGA/VGA adapter has a color resolution of from 16 to 262,144 simultaneous colors. The number of simultaneous colors is related to the number of bits associated with each pixel in the display memory. The more colors used, the more bits required. In both of the EGA/VGA graphics modes used in the software of the present invention (i.e., Modes 10 and 12), the 16 color graphics modes are preferred. In the present invention, there are four bits assigned to each pixel. These four bits are associated with four bit planes. The resolution of the display and the number of bits per pixel determine the total amount of display memory required.

In order to avoid using BIOS calls, colors are controlled by directly placing an appropriate value in the lower four bits of the Map Mask register on the EGA/VGA board. These four bits correspond to red, green, blue and their intensity; therefore, a total of sixteen colors are available.

The Map Mask register is accessed through the I/O (Input/Output) ports. The software can specify which of the four bit planes need to be written.

Advantageously, the white color set by the EGA/VGA's color plate makes the pixels in the LCD transparent.

4.4 Simulation Algorithms and Routines

4.4.1 The Animation Algorithm

In a preferred embodiment, the simulated leukocytes (SLs) will be presented to the observer in an animated form. As is well known, movies and television works animate scenes by displaying sequences of display frames with minute differences between them. These minute changes from frame to frame blend into smooth motion when many frames are sequentially displayed at rates of over 15 frames per second. By the same principle, in the present invention the SL's animation is generated by displaying different frames one after the other on the LCD panel.

In computer animation, two important elements enter into frame rate calculations: frame-to-frame flicker and frame-to-frame discontinuity. It takes time to erase and redraw a screen image; if the screen off interval is a large percentage of the display interval, flickering will result. Furthermore, the interval between two adjacent frames and the duration of a frame must be properly arranged in order to prevent the viewer from observing any discontinuity or flickering.

On a bit plane, each pixel is represented by a display memory bit. In the simulation system of the present invention, the computer generates an image on the display screen by turning on pixels and their corresponding color masks. The entire display RAM (i.e., the image buffer) needs to be cleared before a new image is generated. It is more efficient to draw the pixel that is at foreground. Due to the lack of hardware graphics support in a PC, the PC's speed is often insufficient to plot a frame and to erase it before the next frame is plotted. Flickering often occurs if there is a moment when the screen is blank.

One of the objectives for the present invention is that it should not use any additional graphics support hardware. This objective is achieved by employing better programming techniques and an efficient animation algorithm to boost performance. In computer graphics, many animation algorithms have been developed, depending on different applications and platforms. Because of the random nature of the blue field image and the limited PC graphics hardware resources being used, the doubling image buffer algorithm (full-frame refresh) is used in the present invention to furnish the animation. Under this algorithm, there are two frames that correspond to two pages in the display memory. The screen displays one frame from the first page (the viewed image) while the erasing and drawing are performed on the second page (the virtual image) which is currently invisible. After the drawing is completed on the second page, it will be displayed on the screen to replace the first page. The current displayed page is then made invisible.

Figure 11:
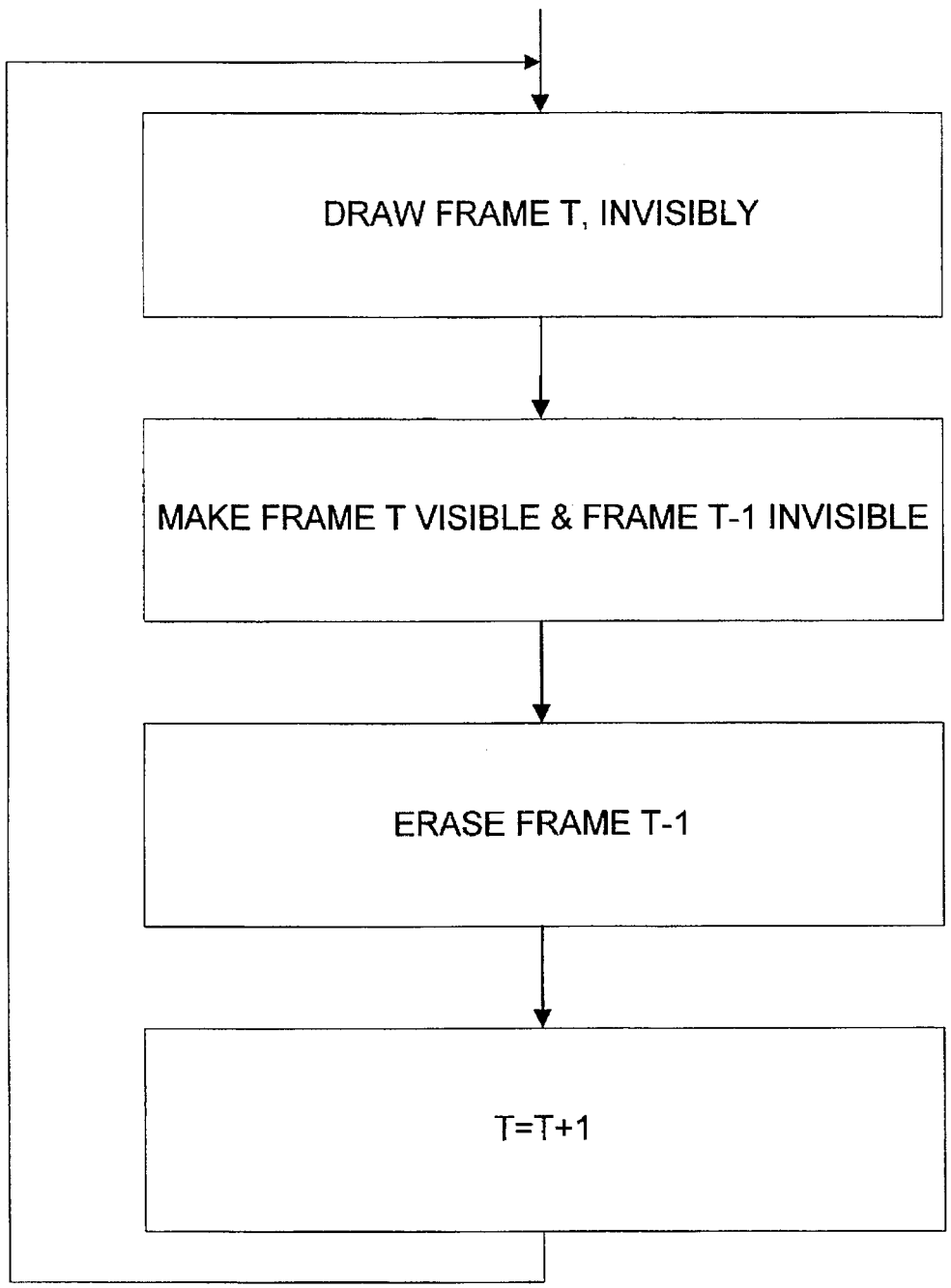
FIG. 11 is a flow chart representing a two frames animation algorithm.

The flow chart for this algorithm is shown in FIG. 11. The algorithm associated with the software of the present invention comprises the following steps: frame t is plotted invisibly, then frame t−1 which is currently visible is made invisible at the same time that frame t is made visible. Frame t−1 is then erased. Frame t is incremented to frame t+1 and the process cycles back to the beginning again.

The transition from displaying one frame to the other is performed synchronously in the hardware. This synchronization ensures that the screen scan is not disrupted when a scan cycle is not completed, so that no screen flicker caused by scan interruption will occur. The program detects the time when the last horizontal scan line at the bottom of the screen is being scanned. This status is obtained by reading the status of Vertical Display End register on the EGA/VGA card.

4.4.2 SL Path Generation Algorithm

A leukocyte travels along a single retinal capillary. In the blue field phenomenon, only leukocytes are able to be perceived; the capillaries themselves are not seen. In the computer simulation of the present invention, the movement attribute of the SL is constrained to move along an embedded and invisible path. In a preferred embodiment, an SL's length is composed of 50 successive line elements (pixels) and has a length of 13.5 mm on the LCD panel. All SL paths are enclosed within a circular area of 175 pixels of outer radius and 35 pixels of inner radius. The entire circular area is about 11.37 degrees and the inner circular area is about 2.3 degrees. The inner circle, in which there are no paths, is designed to imitate the foveal avascular zone. The effective simulation field contains a total of 373,660 pixels.

Figure 12:
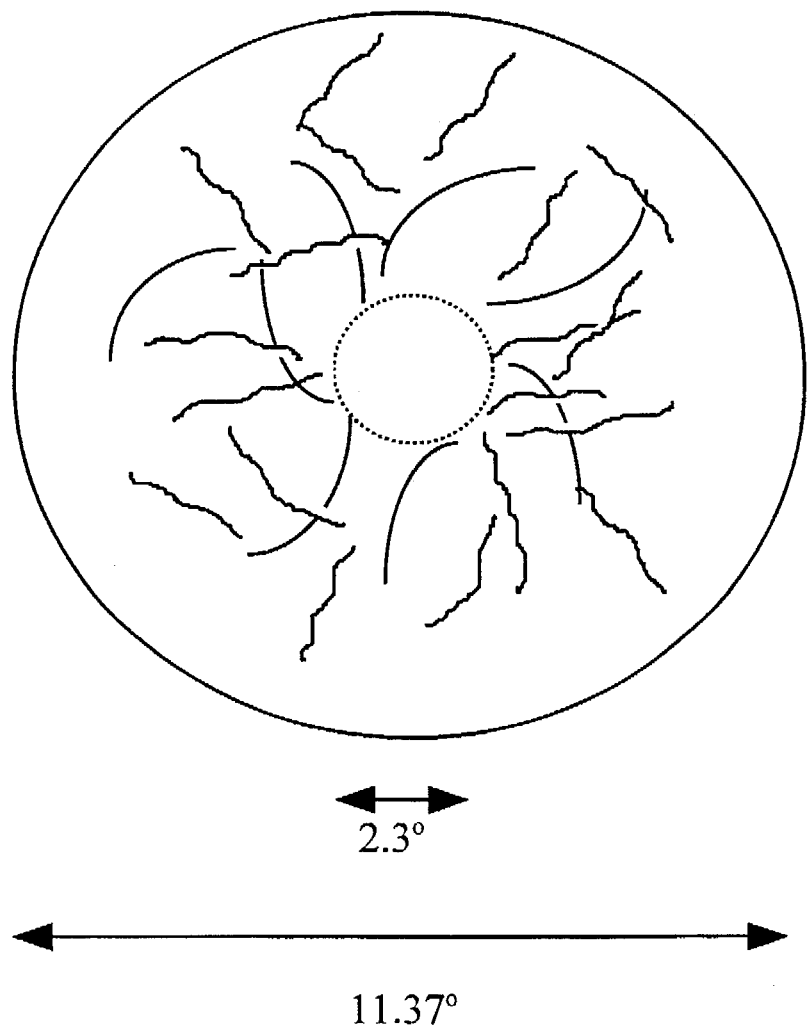
FIG. 12 is an illustration of simulated retinal capillary paths.

The orientations of simulated capillaries (paths) are randomly distributed within a range of 360 degrees. To create those paths, the location of the first pixel of each path is randomly generated. Then, the orientation of the second pixel on the path is randomly picked within the 360 degree range. There are eight possible positions in a range of 360 degrees. A second pixel on a path determines the main orientation of a path. The rest of the pixels in the path are determined randomly within an angle of 4 degrees (clockwise or counterclockwise) relative to their preceding ones. Thus, each path has a curvy shape that is similar to a real retinal capillary. FIG. 12 illustrate an example of simulated capillaries.

Figure 13:
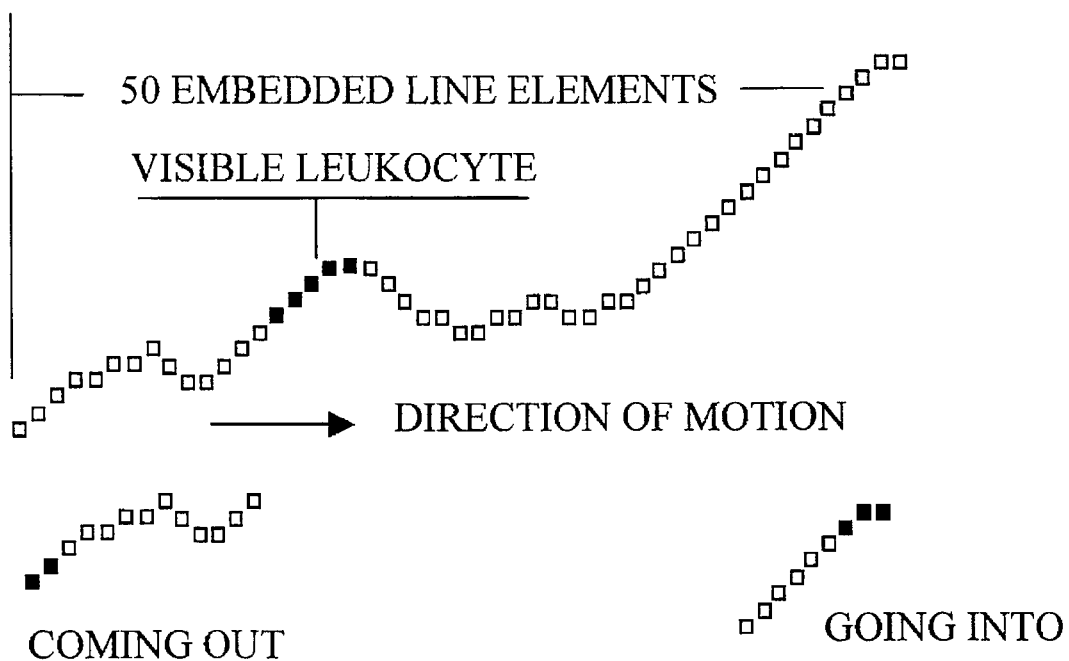
FIG. 13 is a diagrammatic illustration of the structure of an SL's path.

FIG. 13 illustrates a simulated path on the screen. The SL (highlighted pixels) travels from the left end to the right end. On the screen, the position of a pixel may be represented by its vertical and horizontal coordinates (x,y). Therefore, a defined path that includes 50 pixels can be generated and stored as 50 pairs of coordinates. Each pair of coordinates contains two integers, therefore 100 integer numbers are required for each path. In the present invention, this is achieved by using two 2-d arrays, one for x and one for y.

A C program (see Appendix A) was developed to generate a series of data for the paths. To ensure efficiency, several path files were created for different simulation modes. Three to five hundred paths were generated and stored in each data file. Each path has its own unique index code by which it can be retrieved from the data files. The path data files are preferably in an ASCII format. Path data are retrieved by the main program into the arrays for the SL paths.

In the simulation, each SL belongs to a path which is activated. The number of visible SLs is determined by the number of active paths; it can be adjusted by increasing or decreasing the number of active paths. An index variable may be used to determine how many elements in the two arrays need to be retrieved.

A user is able to increase and decrease the number of SLs during the simulation. In one preferred embodiment, the Up-Arrow key and Down-Arrow key on a standard computer keyboard are used to increase or decrease the number of paths being activated.

4.4.3 SL's Motion Algorithm

The velocity of an SL may be considered as a vector. At a specific time, the characteristic of a SL's motion can be described by its direction of motion and its speed. Both direction and speed are time dependent variables. As shown in FIG. 12, an SL moves along a path which regulates its direction. Each path is a one way street; an SL always travels from one end of its embedded path to the other end. At the starting end, the head of the SL is displayed, and then it is shifted from the first pixel to the following ones. This causes the SL to appear to be coming out from the display plane. The heads of the SLs disappear when they reach the last pixel of the paths, so that it looks as though the SLs are going into the display plane and disappearing gradually. After the last pixel, the SL reaches the end of its path, and returns to the beginning of the path.

The speed of an SL is determined by the interval of two sequential frames and the SL's displacement between those two successive frames. The displacement is achieved by moving an SL a certain number of pixels along its path. The number of pixels that an SL skips in one frame interval ($\Delta t$) can be from zero up to fifty pixels. At a same $\Delta t$, the more pixels a SL skips, the faster it travels.

In the blue field, the speed of a retinal leukocyte is perceived in rhythmic accelerations which are synchronous with the heart cycle. The variation of the speed is similar to the typical blood pressure wave. In the present invention, the SL's instantaneous speed is designed to vary so as to mimic the jerky motion caused by a pulse. The SLs' speed model is designed to simulate the blood pressure wave. In a heartbeat cycle, the SL's speed increases sharply from a minimum value to the peak value of systolic velocity. After the speed reaches its peak, it declines gradually and approaches the diastolic velocity. The pulsatility, P, is defined as $1-V_{dis}/V_{sys}$, where $V_{dis}$ and $V_{sys}$ are the diastolic and systolic leukocyte velocities, respectively. In the present invention, P is kept constant and is equal to approximately 0.5.

Figure 14:
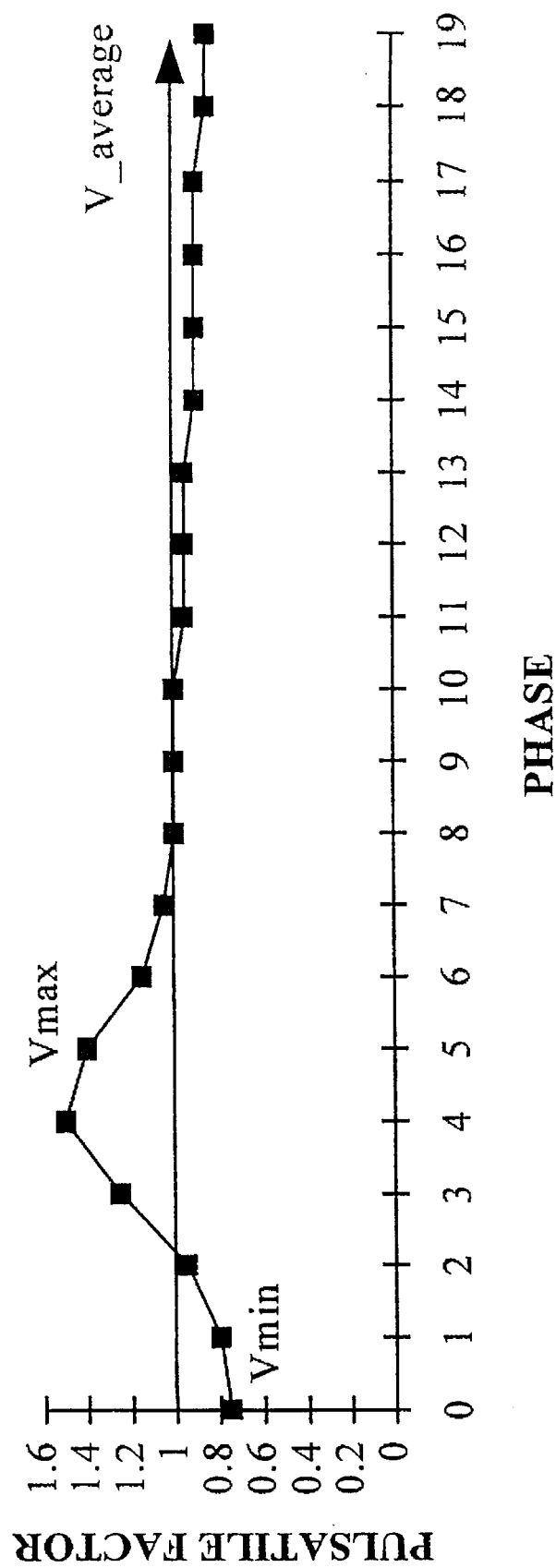
FIG. 14 is a graphical illustration of an instant speed model of an SL.

FIG. 14 shows the numerical model designed for the SL speed simulation. It is preferred to have 20 discrete phases in each cycle. The real cycle duration is determined by the pulse rate. The normalized pulsatile factor has a value of 1 when the speed equals the average speed in one cardiac cycle. The SL speed used in the present invention is always referred to as its average speed. Equation 4.2 gives the algorithm used to determine the displacement of a SL between two consecutive frames. This displacement is a function of average speed, the time interval of two frames and the pulsatile factor.

$$\Delta d_t = speed \times \Delta t \times pulsatile\_factor\ (phase) \qquad (4.2)$$

where $\Delta d$ is the SL's displacement from the previous frame to the current frame; speed is an average traveling speed of the SLs in pixels/second; $\Delta t$ is the time interval between two successive frames; and the pulsatile_factor (phase) is the simulated pulsatile factor based on the model in FIG. 14.

In a preferred embodiment, the value of speed can be adjusted by the Right-Arrow key (increasing) and Left-Arrow key (decreasing). The step size of one key stroke is 0.2 pixels per second. The displacement of a SL on the screen has an integer unit of pixels. To maintain precision, the residual (fraction of a pixel) of the current $\Delta d$ is kept and added to the next displacement calculation. As a result, in the program, equation 4.2 becomes:

$$\Delta d_t = speed \times \Delta t \times pulsatile\_factor(i) + residual\ \Delta d_{t-1}\ \ residual\ \Delta d_t = \Delta d_t - (int)\Delta d_t \qquad (4.3)$$

The interval of two flames ($\Delta t$) varies depending on the complexity of the simulation. The simulation with more SLs or longer SLs takes longer to be completed. In the software of the present invention, there is a timing routine which measures the time between two consecutive frames. Since the PC clock normally only has a resolution of around 50 ms (which is longer than the average blue field simulation cycle), the timing routine reports the measurement for every ten iterations. This means that the program updates the Δt every ten frames. This is not long enough for a human to detect the difference.

At the beginning of the simulation, the initial positions of each of the SLs on their paths are randomly arranged. In the present invention, a data file is created which stores the initial positions for different paths. This data file is created by the program named posinit.c. The position of a SL is defined as its head position on the path, from 0 to 50. Position 0 is the starting pixel of the path and 50 is the end.

4.4.4 Clear Screen Algorithm

Figure 15:
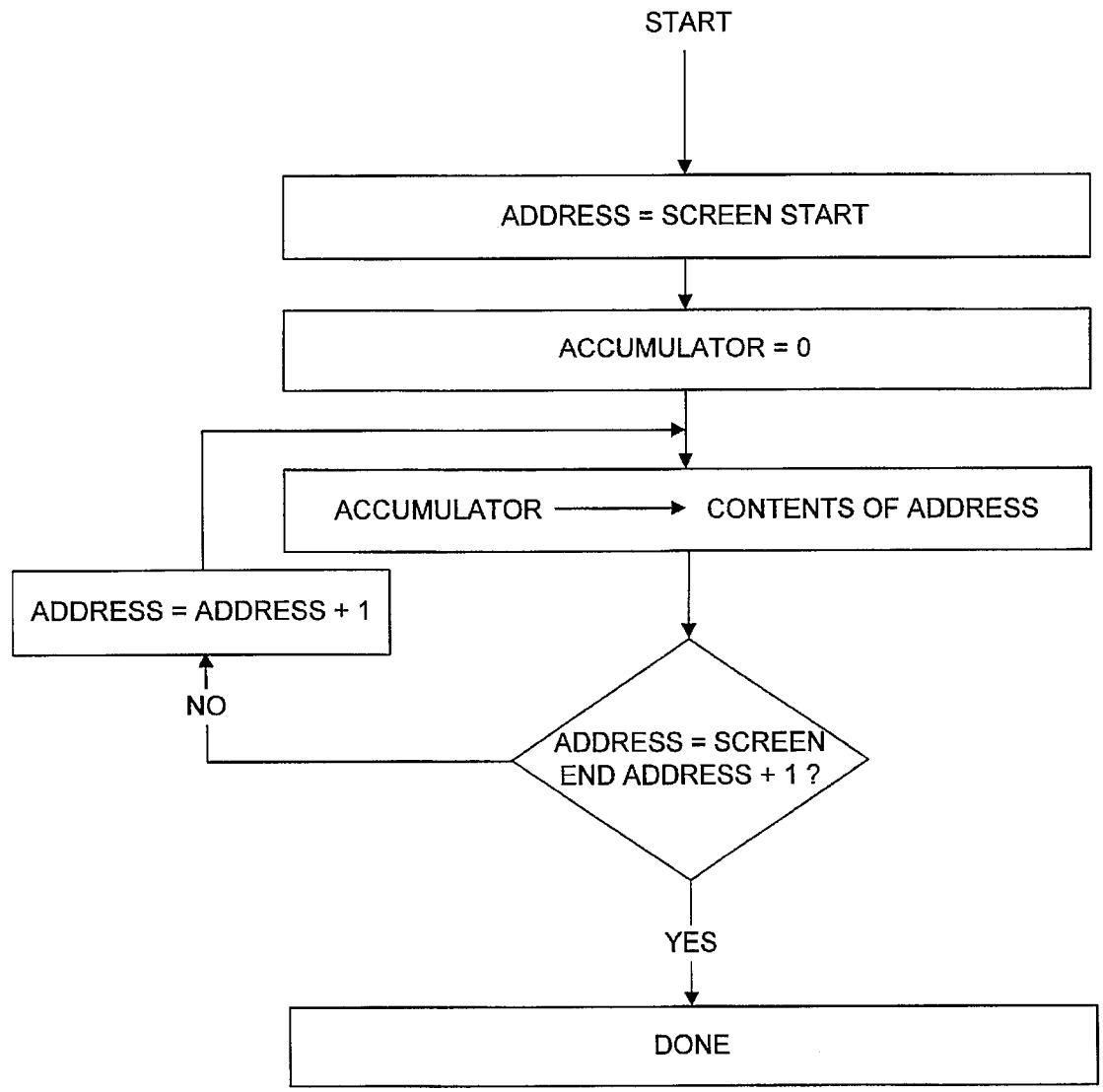
FIG. 15 is a flow chart for a simple memory clear routine used in connection with the present invention.

Before an image is updated, it needs to be erased by first zeroing out its corresponding display buffer page. FIG. 15 is a flow chart of a conventional loop used in the Microsoft C graphics library to clear blocks of memory locations. However, this simple erase loop is relatively inefficient and performs fairly slow erasures. For every byte zeroed, the address counter that points at screen memory must be incremented and checked to see if the full screen is erased yet. A display screen of 640 by 350 resolution contains 28 KBytes &memory, so the memory address updating, checking, and zeroing must be performed twenty eighty thousand times.

It has been found that this routine takes up to 80 ms to perform the erasing on a 386-33 MHz PC. Slow erasing may cause simulation discontinuity. Many graphics intensive computers and workstations provide hardware support for a speedy display memory erasing. Unfortunately, a PC often does not have any such feature. The solution in the present invention is to improve the algorithm.

Figure 16:
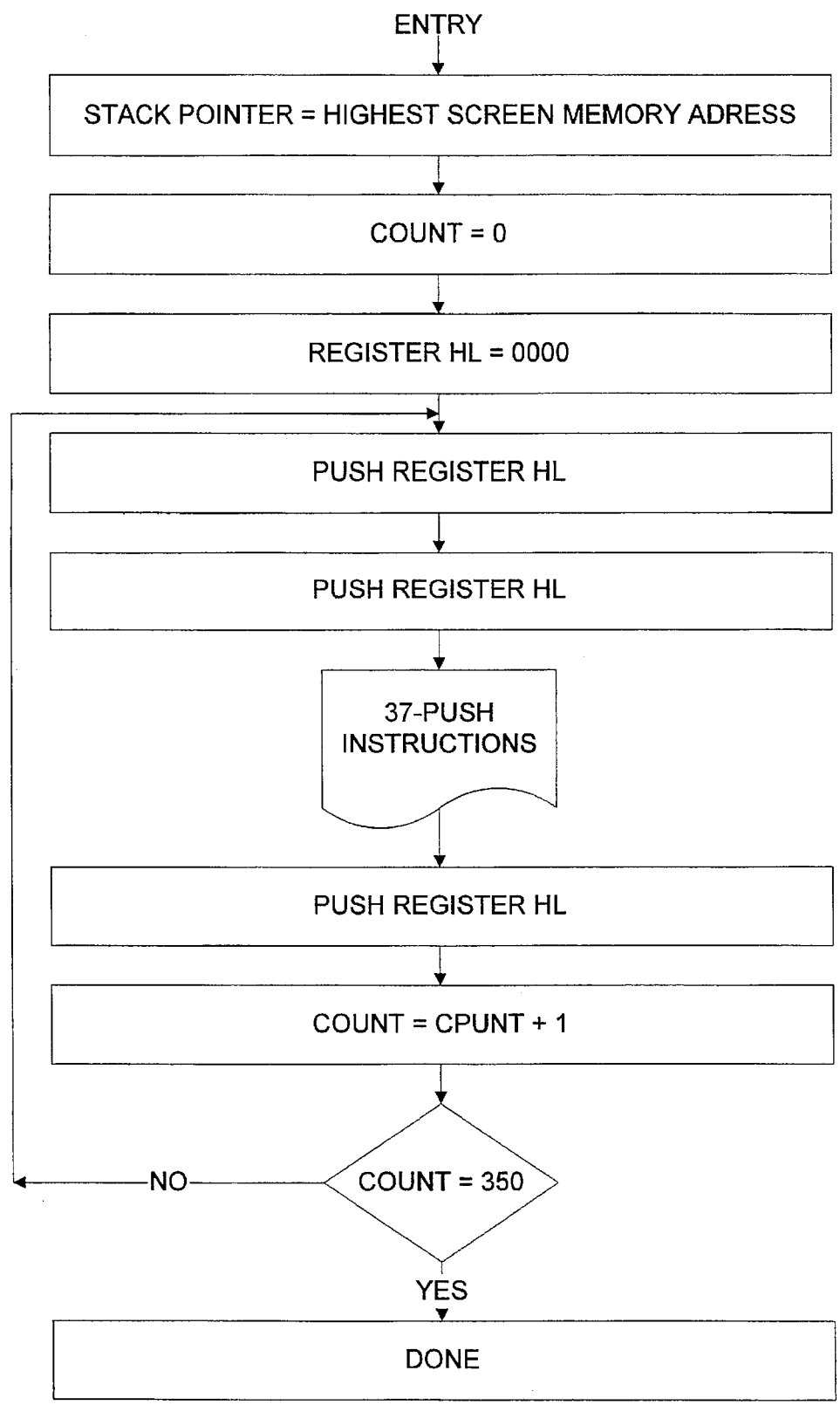
FIG. 16 is a flow chart for a memory clear algorithm based on the PUSH operator.

An erasing algorithm based on PC assembly language instructions has been devised for use in the present invention. In the family of assembly languages, a memory stack operator PUSH was found to be the fastest memory filling instruction on a time-per-byte basis. In addition, the PUSH instruction also automatically updates the address when it is performed. This eliminates the need to increase the address manually. FIG. 16 illustrates a flow chart of this algorithm as implemented in one preferred embodiment of the present invention. First, the stack pointer is positioned at the beginning of each display memory page, then PUSH is executed, rapidly filling the display memory by zero. Each PUSH clears two bytes. The theoretically fastest screen erase routine consists of a long string of the PUSH instructions. In practice, a loop is used to save program space. Instead of putting a single PUSH inside the loop, however, a string of 40 in a row is preferably used. This cuts the loop counting time down by 1/40 of its single-PUSH loop value.

Compared with the aforementioned conventional erasing algorithm, the algorithm of the present invention increases speed by as much as 42%. The screen clear routine is preferably implemented using assembly language.

4.4.5 Memory Direct Access Graphics Primitives

A complicated graphics program is composed of many basic graphic procedures. Such procedures take the coordinates as input and invoke display algorithms to construct a geometric shape on the computer screen or LCD panel.

In the present invention, several fundamental direct display memory access graphical routines are preferred. These routines require considerably less time compared to the same functions that are provided by the standard Microsoft C/C++ graphics library. The colors are accomplished by programming the mask registers in the EGA/VGA controller. To be compatible with standard C graphics routines, the routines of the present invention have been given similar names with an extension of "_bf". These routines also have the same structure of interacting with the calling program. Of course, it will be understood that with slight modifications, these routines can be ported to other platforms or a single chip computer without departing from the scope or spirit of the present invention.

In the following routines, x refers to the column number and y refers to the row number. The uppermost left corner is the origin of x and y (0,0). x and y are integer variables.

4.4.5.1 Move the Current Screen Coordinate (moveto_bf(x,y))

This routine moves the current screen coordinates to the location of x,y. Its function is exactly the same as the routine _moveto(x,y) in the C library. In the program, there is a pair of global integer variables that store the current screen coordinates.

4.4.5.2 Pixel Set & Setoff (setpixel_bf(x,y, pointer), pixeloff_bf(x,y, pointer))

Pixels are the simplest geometric components of a picture. The setpixel_bf(x,y, pointer) and pixeloff_bf(x,y, pointer) are developed to draw or erase a pixel at a specified location on the screen. The position is specified by the column (x) and row (y) variables passed by the calling program. The pointer is the initial display page address. Different display pages take different segments of the display memory and, therefore, have different initial addresses.

The routine calculates the address of the memory byte that contains the memory bit corresponding to the specified screen location, x and y. This address actually is an offset of the initial address. There are 80 bytes across a row, therefore the offset byte address can be obtained by equation 4.31:

$$byte\_address = y*80 + x/8 \qquad (4.31)$$

where y is the row number and x is the column number. In this integer operation, the divide instruction maintains truncation symmetry about the 0 point.

Usually, the division operation takes longer than the bits shifting operation. In the program, equation 4.31 is implemented by right shifting x 3 bits, instead of dividing it by 8.

After the memory byte is located, the routine positions the location of the bit within this byte. This is done by starting with the bit on the left side of the byte, and then fight shifting it, as many times as necessary, to put it in the appropriate place in the byte. The number of times to shift is determined by the remainder operation in C (%):

$$bit\_position = x \div 8 \qquad (4.4)$$

The bit_position is the remainder of x dividing by 8.

Finally, the routine changes the specified pixel only and keeps unchanged the remaining seven bits in the byte being addressed. This is achieved by first reading the byte, then performing AND off (remove) on the bit that needs to be changed, leaving the other seven bits unaltered; then OR on (insert) is performed on the bit. A mask is used to AND off the appropriate bit. The mask is created by fight shifting the constant 0×7f (01111111 binary) bit_position times. An integer variable must be used to guarantee that the 1s will be shifted in on the left.

The color of the pixel is set by the map mask registers through the I/O port. Users can specify the color through the system configuration.

4.4.5.3 Line-drawing (lineto_bf(x,y))

Two positions on the screen can specify a line. As in the standard C line drawing function, this line drawing is accomplished by moving the current screen coordinates to one of the ends of the line being drawn $(x_1, y_1)$. This is accomplished by using the routine of moveto_bf($x_1, y_1$), followed by lineto_bf($x_2, y_2$) to draw the line, where ($x_2, y_2$) is the other end of the line.

The Bresenham's line-drawing algorithm is employed to generate the line. This is an efficient line-drawing algorithm to determine pixel positions. It finds the closest integer coordinates to the actual line path using only integer arithmetic. The procedure of this algorithm is described below:

(1). Input line endpoints. Store left endpoint in $(x_1, y_1)$. Store right endpoint in $(x_2, y_2)$.

(2). The first point to be selected for display is the left endpoint $(x_1, y_1)$.

(3). Calculate $\Delta x = x_2 - x_1$, $\Delta y = y_2 - y_1$, and $p_1 = 2\Delta y - \Delta x$. If $p_1 < 0$, the next point to be set is $(x_1+1, y_1)$. Otherwise, the next point is $(x_1+1, y_1+1)$.

(4). Continue to increment the x coordinate by unit steps. At position $x_1+1$, the coordinate to be selected, $y_1+1$, is either $y_i$ or $y_i+1$, depending on whether $p_1 < 0$ or $p_i >= 0$. The calculations for each parameter p depend on the last one. If $p_i < 0$, the form for the next parameter is $$p_{i+1} = p_i + 2\Delta y$$

But if $p_i >= 0$, the next parameter is $$p_{i+1} = p_i + 2(\Delta y - \Delta x)$$

Then, if $p_{i+1} < 0$, the next y coordinate to be selected is $y_{i+1}$. Otherwise, select $y_{i+1}+1$. (Coordinate $y_{i+1}$ was determined to be either $y_i$ or $y_{i+1}$ by the parameter pi in step 3.)

(5). Repeat the procedures in step (4) until the x coordinate reaches $x_2$.

This routine needs to call the pixel set routine: setpixel_bf(x,y, pointer).

4.4.5.4 Circle-Generating (circle_bf($x_1, y_1, r$))

The circle generation routine is based on Bresenham's circle algorithm. To plot a circle, the position of the center $(x_1, y_1)$ and the radius (r) need to be passed to the routine. The procedure to generate the circle is listed as follows:

(1). Select the first position for display as $$(x_1, y_1) = (0, r)$$

(2). Calculate the first parameter as $$p_1 = 3 - 2r$$

If $p_1 < 0$, the next position is $(x_1+1, y_1)$. Otherwise, the next position is $(x_1+1, y_1-1)$.

(3). Continue to increment the x coordinate by unit steps, and calculate each succeeding parameter p from the preceding one. If for the previous parameter we found that $p_i < 0$, then $$p_{i+1} = p_i + 4x_i + 6.$$

Otherwise (for $p_i >= 0$), $$p_{i+1} = p_i + 4(x_i - y_i) + 10$$

Then, if $p_{i+1} < 0$, the next point selected is $(x_i+2, y_{i+1})$. Otherwise, the next point is $(x_i+2, y_{i+1}-1)$. The y coordinate is $y_{i+1} = y_i$, if $p_i < 0$ or $y_{i+1} = y_i - 1$, if $p_i >= 0$.

(4). Repeat the procedures in step 3 until the x and y coordinates are equal.

4.4.5.5 Crosshair ()

On the simulation screen of the present invention, there is a cross at the center that divides the field into four symmetric quarters. This crosshair is composed of one vertical and one horizontal broken line, in light gray color. The broken line has elements consisting of eight pixels, eight pixels on and eight pixels off alternatively. The routine needs to be called at every updating frame; therefore its execution speed is very important. No variables need to be passed because the routine always places the crosshair in the center of the field.

4.5 Program Structure

The software system of the present invention comprises 11 modules. Each module delivers its individual function. FIG. 16A lists all of these modules and their functionality. The first six modules are blue field simulation modes with different simulation techniques. Module 7 is for FAZ simulation and FAZ dimension estimation. It needs to be coupled with the hardware installation of the AVMEI. The rest of the modules are for data management and processing. All of these modules are integrated by an interactive GUI.

Figure 17:
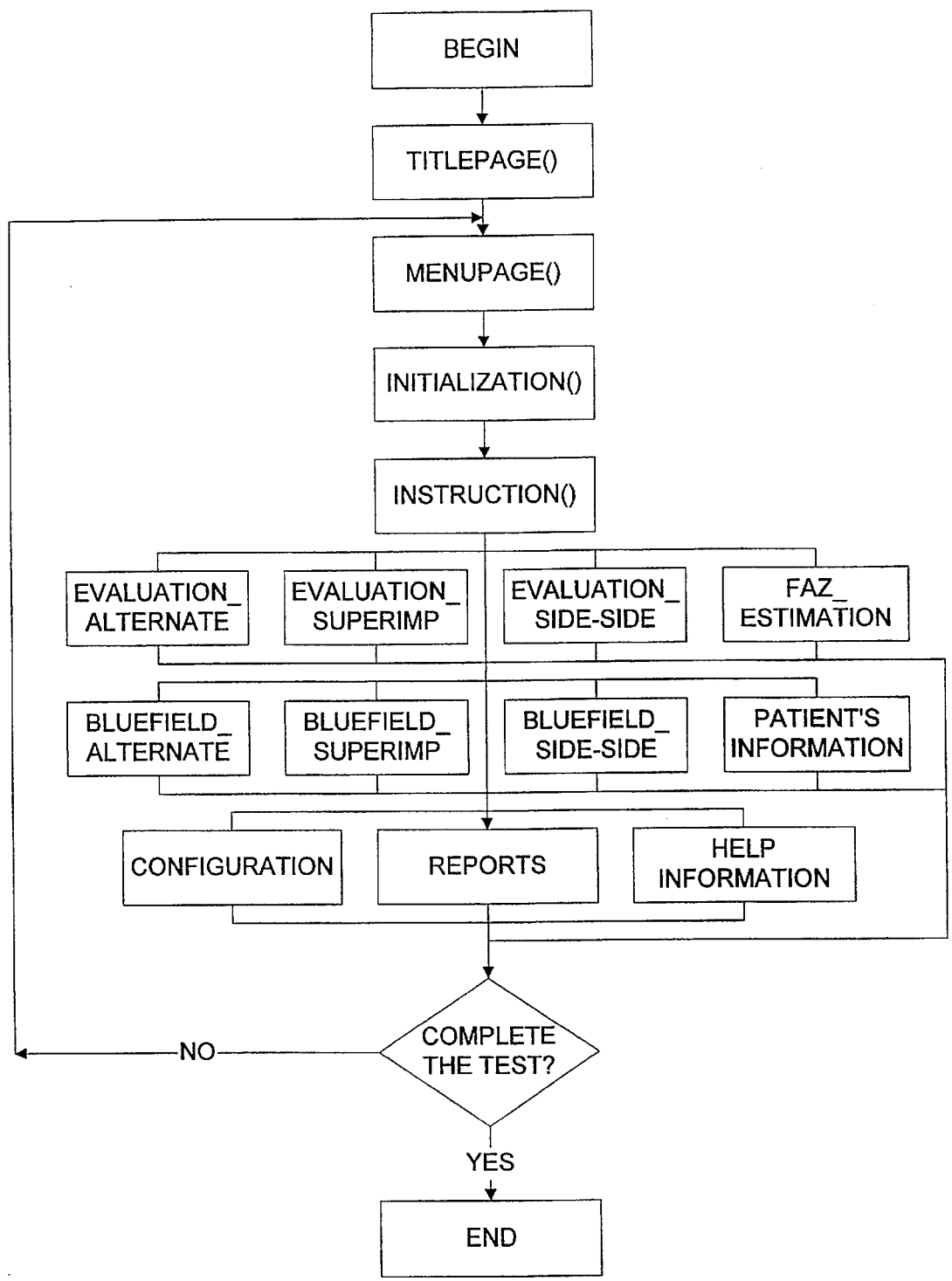
FIG. 17 is a flow chart of the general program structure for the software used in connection with the present invention.

The flow chart for the upper level structure of the program is illustrated in FIG. 17. The software determines the current operation mode according to the status of a global variable that is set by the user through the GUI. Upon completion of the job at the current module, the program returns to the menu page where a new module is to be selected.

4.6 Interactive GUI

The GUI is developed to integrate all the program modules and provide an easy access to these modules, for the user performing the test as well as the medical personnel analyzing the data.

Figure 18:
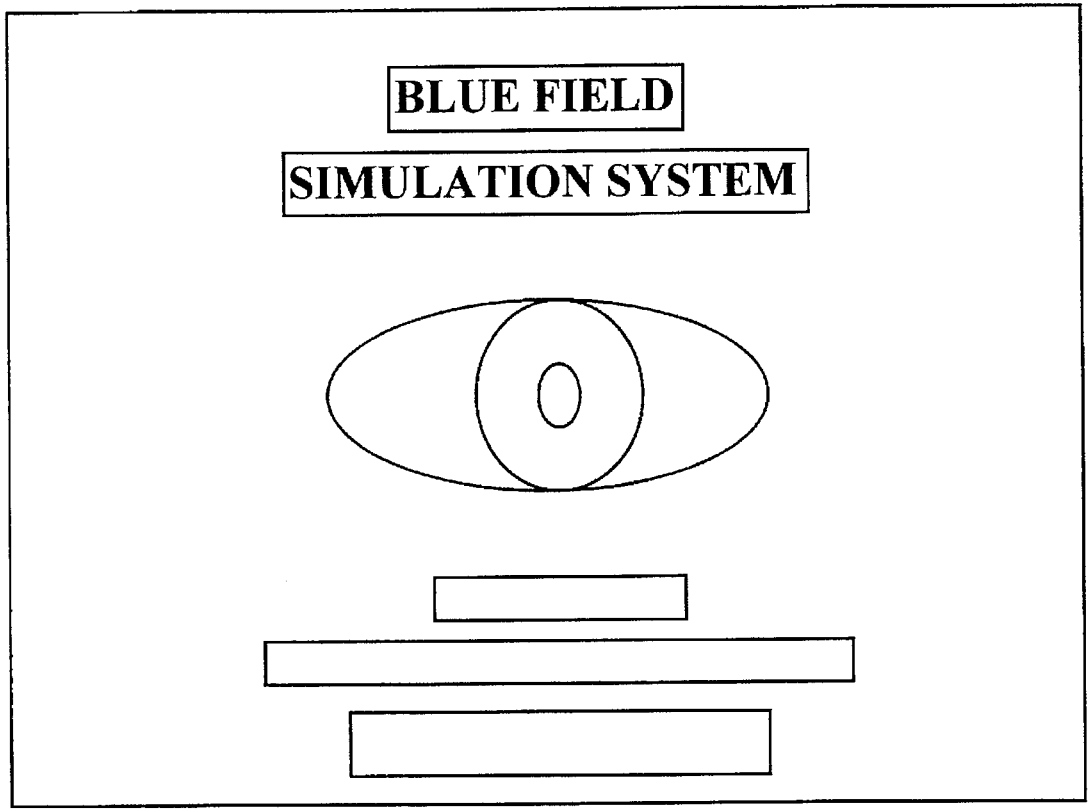
FIG. 18 is a diagrammatic illustration of the title page as created by the software of the present invention.
Figure 19:
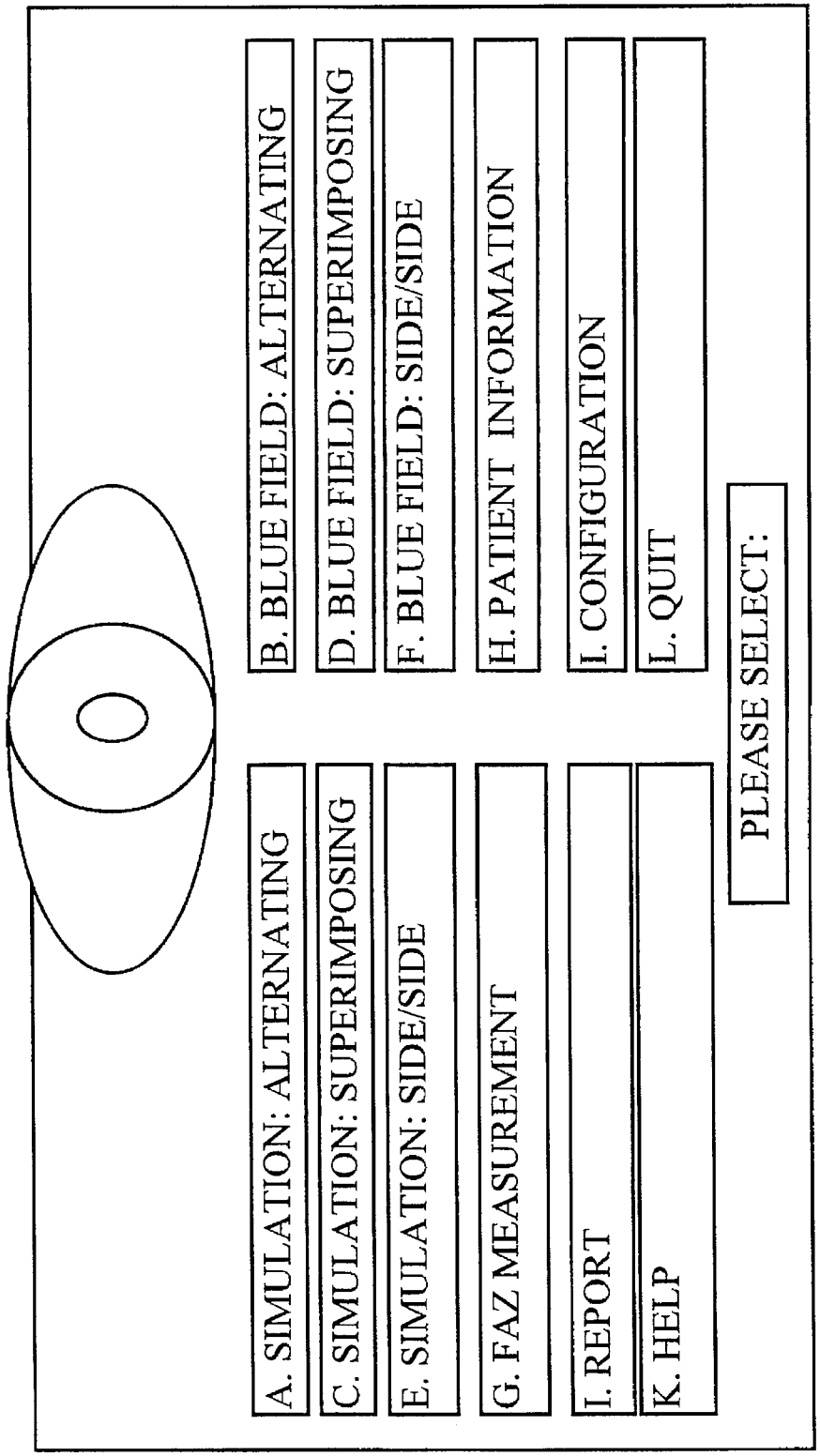
FIG. 19 is a diagrammatic illustration of the menu page as created by the software of the present invention.

Upon execution of the program, a title page (FIG. 18) is presented to the user. This page gives general information and displays the system logo on a light blue background. After five seconds, or when any key is hit, the title page is replaced by a menu page (FIG. 19) which includes the list of all the operational modules that the program supports, plus the Exit function which terminates the program. Users can select one of the modules by typing its call letter.

Figure 20:
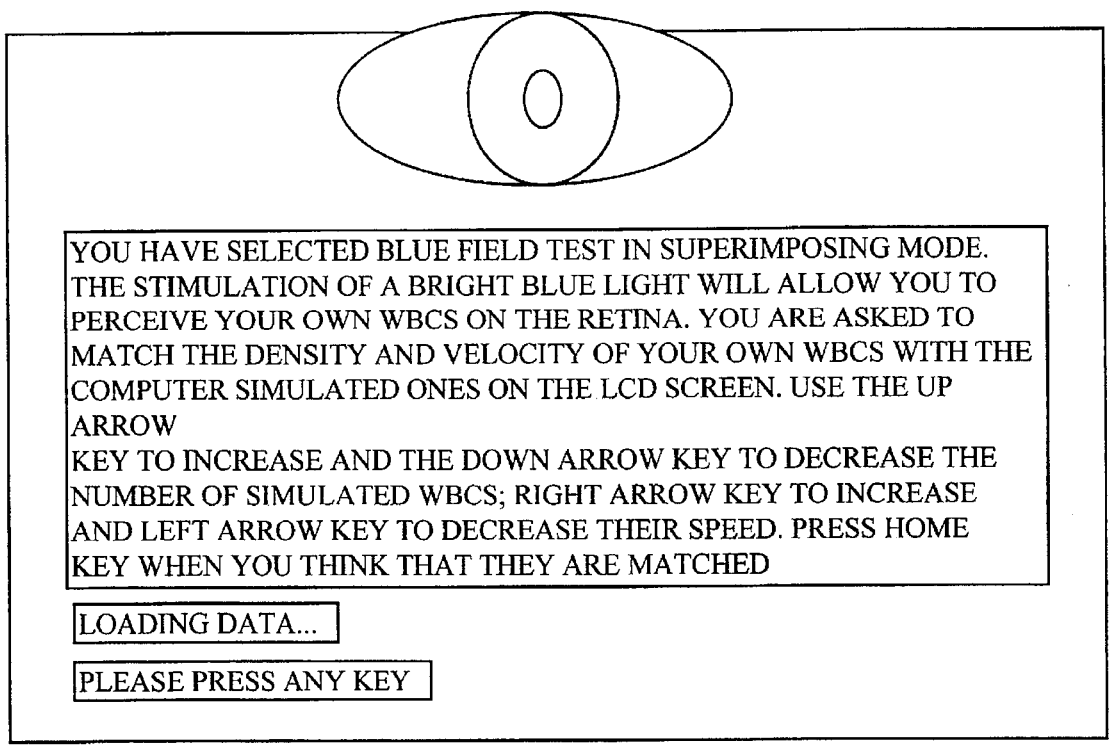
FIG. 20 is a diagrammatic illustration of the transitional page for a superimposing blue field test, as created by the software of the present invention.

If one of the simulation modules is selected, the program switches to a transitional page (FIG. 20) while the data are being retrieved from the disk data files. On the transitional page, a brief operation instruction on the selected module is presented. The simulation starts after users read the instruction and hit a key. The data loading takes about 5 seconds on a 386 PC (33 MHz). The simulation returns to the menu page after the number of trials reaches the repetition number that is set by the system configuration. In the Patient Information and Configuration modules, related variables and their current settings are listed. Users can use four arrow keys to move the cursor and highlight the variable that needs to be modified. Pressing the Esc key will save these modified variables and return the user to the menu screen.

The font used in the GUI is provided by the modern.fon. This font file is resident in the current disk directory. At the beginning of the execution, the program initializes the fonts graphics system and registers the Modern font for font-related library function. Modern.fon provides a vector font so that the width and height of the characters can be changed.

4.7 Program Modules

4.7.1 Evaluation Tests

Under evaluation tests, there are two simulation fields: the reference field and the test field. The subject adjusts the parameters of SLs in the test field so that they match the present SLs in the reference field. The parameters of the SLs in the reference field, such as numbers, speed, color and lengths, are pre-set by the operator in the system configuration. The subjects are neither informed of, nor allowed to access, these settings during the test.

The color of the SLs in the test field are white. Before operation, subjects are asked to select the color that is most distinguishable to white for SL's in the reference field. In a preferred embodiment, there are 14 different colors available for the SLs in the reference. Both the reference and the test fields have the same blue background.

The test field starts with a random number of simulated leukocytes, each having random speed. The range of initial numbers of SLs is from 0 to 120, and the initial speed is from 0 to 5.7 mm/s. The randomizations are uniformly distributed. The number and the speed can be adjusted through keys on the host computer keyboard. The Up-Arrow key and Down-Arrow keys are used to increase and decrease the number of SLs, respectively. The step size for changing number is 2; this means every time the Up-Arrow or Down-Arrow key is hit, the number of SL's on the screen will be increased or decreased by two. The Right-Arrow is used for increasing the speed and Left-Arrow key is used for decreasing the speed of the SLs. The speed changing resolution is about 0.05 mm/s at retina.

Upon completion of the matching process, the Esc key is used to terminate the current test session and record the results in a disk data file.

4.7.1.1 Alternating

In this module, the reference and the test fields are exhibited one at a time, in substantially the same manner as the prior art. After entering this module, the reference field will be presented first. The number and speed of the SLs are the same as the values in the system configurations. The Page-Up key is used to switch between the reference field and the test field. This key is programmed as a toggle switch. The matching process is performed by switching between the two fields and adjusting the speed and the number of SLs in the test field. The adjustment keys are only active when the test is displayed.

There are no limits for the number of times that a subject can switch between the two fields.

4.7.1.2. Superimposing

In this module, SLs in the reference field and the test field are intermixingly displayed on the same screen simultaneously. No switching between the two fields is necessary. The SLs in the two fields are distinguished by their colors. The SLs in the test field are always in white.

4.7.1.3 Side-by-Side

In the side-by-side module, the screen is vertically split into two segments. The left half is the reference field and the right half is the test field. Different colors are assigned to the SLs in the two fields. The matching procedure is the same as above.

4.7.2 Blue Field Tests

After the user completes the desired evaluation tests, they can proceed to performing an actual blue field simulation test. The actual blue field stimulation and measurement of the observer's own leukocytes are conducted in the blue field simulation tests. A patient adjusts the number and velocity of SLs in the test field to match his own leukocytes perceived in the blue field entoptic phenomenon. As in the evaluation test modules, the initial number and speed of SLs in the test field are initially randomized for each trial.

4.7.2.1 Alternating

Under this mode, the LCD in the present invention will have a transparent circular area first. This transparent circular area allows the blue light to project on the retina of the subject so that the blue field entoptic phenomenon can be elicited. The Page-Up key is used to switch to the test field where white SLs are presented at a dark background. Therefore, the matching between the leukocytes perceived in the blue field and the SLs presented in the test field can be performed in the same way as the alternating evaluation tests, except that the subject will be matching against their own real leukocytes perceived under the blue light phenomenon. The program permits subjects to swap between the blue field and the test field as many times as they want to.

4.7.2.2 Superimposing

In the superimposing blue field test, the program generates the dark SLs on a transparent background which lets the blue light transmit to the viewer. This setup allows the viewer to see both dark SLs on the LCD and the stimulated retinal leukocytes simultaneously. The adjustment keys for the SLs are constantly monitored during the simulation.

4.7.2.3 Side-by-Side

In side by side operation, the program keeps the left half circular area of the LCD transparent. Therefore the viewer is able to perceive the blue field phenomenon at his left half of the visual field. The adjustable white SLs with a dark background are displayed at the right half circular area on the LCD. The dark background blocks the light and allows the viewer to see those SLs only.

4.7.3 FAZ Measurement

In order to measure the FAZ, the LCD is programmed to provide a circular transparent area, so that a uniformed blue background is provided for AVMEI. On the center of this circular area, there is a red ring whose radius can be adjusted. The Up-Arrow and the Down-Arrow keys are used to increase and decrease the radius of this ring respectively. The step size of the radius adjustment is one pixel (0.27 mm) on the LCD. The subject measures the size of the FAZ by matching the size of the ring to the FAZ perceived under the stimulation of the AVMEI.

4.7.4 System Configuration

In a system configuration mode, the program of the present invention interacts with the user to set the system parameters and operation variables. The color, size, number and speed of the SLs in the reference field are selected in the system configuration. Other system variables such as the distance between the LCD and the viewer, the number of trials for each test, etc. are also set at this system configuration. The program provides an interactive GUI for users to access those values and make changes. There are range limits assigned for those parameters and variables and a warning signal will be given if an illegal entry occurs.

4.7.5 Patient Information

The patient information module is used to prepare a report. The program stores the information such as patient name, age, gender, the eye being tested, the IOP, blood pressure and pulse rate, etc. This information is input and modified by an interactive GUI.

4.7.6 Report

Figure 21:
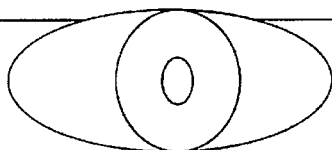
FIG. 21 is a diagrammatic illustration of a report for the evaluation test as created by the software of the present invention.

The experimental conditions, the test data and the aggregated results are contained in a report screen. The detail information such as the test mode, the date, the starting and finishing time, the parameters in reference field, the scrambled initial values, the tests results and the cumulated average are included in the report. FIG. 21 illustrates a sample page of the report for a superimposing evaluation test.

On the first line of the report screen, the name of the patient is printed, followed by the mode of the testing, and the time and the date of the test. Thereafter, information on each trial is given and the raw data are tabulated.

The column labels are defined as follows:

TriNum: the total number of trials performed;

Tm: the time when the matching is completed;

Ref.N: the number of SLs in the reference field;

TestN: the number of SLs in the test field;

N-Ave: the cumulative average number in test field across trials;

Ref.V: the velocity of SLs in the reference;

Test.V: the velocity of SLs in the test field;

V-Ave: the cumulative average velocity in the test field across trials;

Init.N: the randomly scrambled initial number in the test field;

Init. V: the randomly scrambled initial velocity in the test field;

Ref.N and Ref.V are only available in the evaluation tests. The initial values provide the information on how much effort is needed to perform the matching.

The results are aggregated in the summary section on the report sheet. The summary includes the mean, the standard deviation and the coefficient of variation in percent. The coefficient of variation is an indication of the precision of the results. In the case of the evaluation tests, additional information is summarized to examine the accuracy of the testing results. The normalized value for the number and the velocity are defined by equation 4.5 and 4.6.

$$\text{Normalized Number} = N_{test}/N_{ref} \quad (4.5)$$

$$\text{Normalized Velocity} = V_{test}/V_{ref} \quad (4.6)$$

where $N_{test}$ and $V_{test}$ are the matching results of number and velocity; and $N_{ref}$ and $V_{ref}$ are the number and velocity in the reference field, respectively. The accuracy of the results for the evaluation tests can be obtained from the deviations between the normalized result and the value of 1.

The following page of the report scrolls in when a key is hit. The Esc key is used to terminate the report and return to the menu pages. All the report information is stored in an ASCII file (report.dat) which can be edited and printed.

4.7.7 Help

The help function is designed to provide guidance for users operating the program. There is a text file containing different blocks of the help information regarding various operation modes. These text blocks are indexed for the program to search and retrieve. When a particular operating mode is selected, a brief instruction will be displayed on the screen while the program is loading the simulation data files into memory.

The "Help" mode in the menu page provides general information about the operation of the program.

All help information is displayed on the top of the system background in a graphics text mode.

4.8 Data Storage and Process

In the present invention, there is a disk data log file used to store all the results and system variables. This data file is preferably in ASCII format and named through the system configuration. Every time the patient completes a trial (i.e., when the Esc key is pressed), the information such as the test mode, the time, the date, the trial number, the number and the speed of SLs in the reference field (for evaluation tests), the number and speed of SLs in the test field (for actual testing), the initial test number and test velocity and the interval of two frames are stored in this disk data file. Each trial stores as one record.

The file name is preferably related to the patient's name.

4.9 System Data Files and Installation

In order to improve programming efficiency and save memory space, 10 data files are included in the software system of the present invention. The program only interacts with those data files that are related with a current operation mode. The memory residence of these files is cleared after they are used. An error message will be given if one of these files is missing from the current directory. The missing file name is included in the error message.

FIG. 22 is the list of these data files and their functions. The first 9 files are in ASCII format and the last one is a Binary file. In the column of type, R means a read only file; W is a write only file; and R/W is both a write and read file.

ALTERNATIVE EMBODIMENTS

It is also known that changes in retinal blood flow may be deliberately induced in the observer by causing the blue field to flicker. To that end, computer 60 may be programmed so as to cause LCD panel 45 to act as a shutter. In particular, computer 60 may be programmed so as to cause LCD panel 45 to become opaque; then to restore itself so as to create the simulated leukocytes in the manner discussed above; then to go opaque again, etc., in the manner of a blinking shutter. This will result in the desired flicker effect needed to induce changes in the observer's retinal blood flow. At the same time, however, the changes in that observer's retinal blood flow may be observed using entoptoscope 25 in the manner discussed above.

Figure 23:
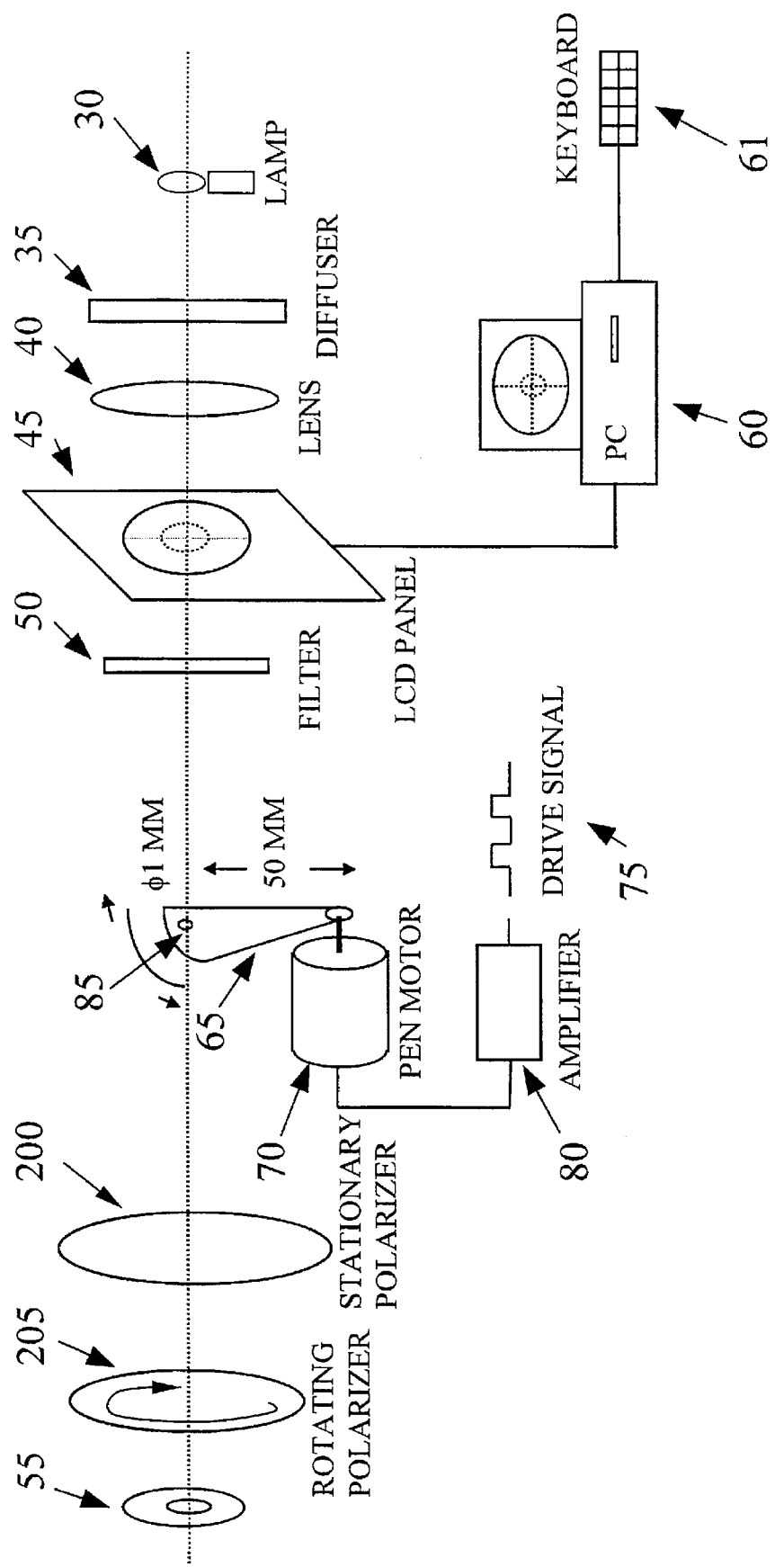
FIG. 23 is a schematic view of another embodiment of the optical setup of the present invention.

Alternatively, if preferred, the blue light flicker may be caused by introducing additional flicker-inducing elements of the sort well known in the art into the entoptoscope of the present invention, e.g., by positioning appropriate polarizers in the optical path so as to modulate the level of light impinging upon the observer. See, for example, FIG. 23, which shows a pair of conventional light polarizers 200 and 205, wherein polarizer 200 is stationary and polarizer 205 is rotating, whereby polarizers 200, 205 can together modulate the level of light impinging upon the observer.

ADVANTAGES OF THE INVENTION

Numerous advantages are obtained by employing the present invention.

More specifically, an improved ophthalmic diagnostic device is provided that significantly increases the reliability of the results obtained when conducting blue field entoptic diagnostic procedures.

In addition, an improved ophthalmic diagnostic device is provided that is adapted to compare entoptically observed corpuscles with computer simulated images of corpuscle-like particles without requiring the observer to view more than one screen.

Furthermore, the present invention provides a novel ophthalmic diagnostic device and method which do not rely upon the short term memory of the observer.

Also, a novel ophthalmic diagnostic device is provided that operates under the control of a relatively inexpensive personal computer.

Furthermore, the present invention provides a novel ophthalmic diagnostic device and method that will yield reliable results with a broader range of patients.

In addition, the present invention provides a novel ophthalmic diagnostic device and method that reduces the time required to make a reliable diagnosis.

Another advantage of the present invention is the provision of a novel ophthalmic diagnostic device and method for determining the size and speed and pulsatility of leukocytes within the retinal capillaries of an observer.

In addition, the present invention provides a novel ophthalmic diagnostic device and method for determining and documenting the size of the foveal avascular zone (FAZ).

Furthermore, the present invention provides a novel ophthalmic diagnostic device and method for determining changes in the observer's leukocyte characteristics due to flicker stimulation.

Also, the present invention provides a novel ophthalmic diagnostic device which is smaller in size than prior art devices.

The present invention also provides a novel ophthalmic diagnostic device which is less expensive than prior art devices.

The present invention may, of course, be embodied in other specific forms without departing from the spirit or essential characteristics of the invention. The present embodiments and examples are, therefore, to be considered in all respects as being illustrative and not restrictive, with the scope of the present invention being indicated by the claims rather than by the foregoing description. All changes that come within the meaning and range of equivalency of the claims are therefore intended to be embraced therein.

What is claimed is:

1. An apparatus for determining the number and speed and pulsatility of entoptically observed leukocytes in the retinal capillaries of an observer, said apparatus comprising:

display means for displaying a plurality of simulated leukocytes within the visual field of said observer whereby said entoptically observed leukocytes are observed simultaneously with, and in the same visual field as, said simulated leukocytes, said display means comprising a first side and a second side, wherein said display means are adapted to transmit light from at least one of said sides thereof, and further wherein said display means is adapted to be controlled by a programmable computer of the sort comprising user input controls such that said observer can adjust the number and speed and pulsatility of said simulated leukocytes so as to compare said simulated leukocytes with said entoptically observed leukocytes;

a source of illumination disposed in spaced relation to said observer, said display means being positioned between said source of illumination and said observer, so that said first side of said display means faces said source of illumination;

filter means disposed in front of said second side of said display means, said filter means being adapted to restrict the wavelength of incident light that is emitted from said display means to a predetermined wavelength whereby said observer will experience the blue field entoptic phenomenon; and means for viewing said display means through said filter.

2. Apparatus according to claim 1 wherein said apparatus further comprises a moving artificial pupil disposed between said light source and said observer, whereby said observer will experience the Perkinje phenomenon.

3. Apparatus according to claim 2 wherein said artificial pupil is adapted to follow a linear motion.

4. Apparatus according to claim 2 wherein said artificial pupil is adapted to follow a circular motion.

5. Apparatus according to claim 1 wherein said apparatus further comprises a means for selectively interrupting light reaching said observer from said light source, whereby said observer will experience the flicker effect of the blue field entoptic phenomenon.

6. Apparatus according to claim 5 wherein said apparatus further comprises a rotating polarizer filter disposed between said light source and said observer so as to cause said light reaching said observer to flicker.

7. Apparatus according to claim 1 wherein said display means comprise a liquid crystal display.

8. Apparatus according to claim 7 wherein said liquid crystal display is at least partially transparent to incident light.

9. A method for determining the number and speed and pulsatility of entoptically observed leukocytes in the retinal capillaries of an observer, said method comprising the steps of:

(A) providing an entoptoscope adapted to elicit blue field entoptic phenomena in the mind of the observer, said entoptoscope comprising:

display means for displaying a plurality of simulated leukocytes within the visual field of said observer whereby said entoptically observed leukocytes are observed simultaneously with, and in the same visual field as, said simulated leukocytes, said display means comprising a first side and a second side, wherein said display means are adapted to transmit light from at least one of said sides thereof, and further wherein said display means is adapted to be controlled by a programmable computer of the sort comprising user input controls such that said observer can adjust the number and speed and pulsatility of said simulated leukocytes so as to compare said simulated leukocytes with said entoptically observed leukocytes;

a source of illumination disposed in spaced relation to said observer, said display means being positioned between said source of illumination and said observer, so that said first side of said display means faces said source of illumination;

filter means disposed in front of said second side of said display means, said filter means being adapted to restrict the wavelength of incident light that is emitted from said display means to a wavelength of about 430 nanometers; and means for viewing said display means through said filter;

(B) observing said source of illumination through said display means and said filter and displaying images of said simulated leukocytes on said display means so that said simulated leukocytes are observed simultaneously with, and in the same visual field as, said entoptically observed leukocytes; and (C) adjusting the number and speed and pulsatility of said simulated leukocytes using said user input controls so as to match the number and speed and pulsatility of said entoptically observed leukocytes.

10. A method for determining the foveal avascular zone in the retina of an observer, said method comprising the steps of:

(A) providing an entoptoscope adapted to elicit blue field entoptic phenomena in the mind of the observer, said entoptoscope comprising:

display means for displaying a circle of variable size within the visual field of said observer simultaneously with, and in the same visual field as, said foveal avascular zone, said display means comprising a first side and a second side, wherein said display means are adapted to transmit light from at least one of said sides thereof, and further wherein said display means is adapted to be controlled by a programmable computer of the sort comprising user input controls such that said observer can adjust the size of said circle so as to compare said circle with said entoptically observed foveal avascular zone;

a source of illumination disposed in spaced relation to said observer, said display means being positioned between said source of illumination and said observer, so that said first side of said display means faces said source of illumination;

filter means disposed in front of said second side of said display means, said filter means being adapted to restrict the wavelength of incident light that is emitted from said display means to a selected wavelength; and means for viewing said display means through said filter;

(B) observing said source of illumination through said display means and said filter and displaying a circle of variable size on said display means so that said circle is observed simultaneously with, and in the same visual field as, said foveal avascular zone; and (C) adjusting the size of said circle using said user input controls so as to match the entoptically observed foveal avascular zone.

11. An apparatus for determining the number and speed and pulsatility of entoptically observed leukocytes in the retinal capillaries of an observer, said apparatus comprising:

an appropriate source of illumination disposed in spaced relation to said observer;

display means for displaying a plurality of simulated leukocytes, said display means being positioned between said source of illumination and said observer, and said display means being capable of selectively passing light therethrough or selectively blocking light from passing therethrough, said display means being adapted to display said simulated leukocytes within the visual field of said observer whereby said entoptically observed leukocytes are observed simultaneously with, and in the same visual field as, said simulated leukocytes, and further wherein said display means comprise user input controls such that said observer can adjust the number and speed and pulsatility of said simulated leukocytes so as to compare said simulated leukocytes with said entoptically observed leukocytes; and means for restricting the wavelength of light impinging upon said observer from said source of illumination to a predetermined wavelength, whereby said observer will experience the blue field entoptic phenomenon.

12. Apparatus for determining the number and speed and pulsatility of entoptically observed leukocytes in the retinal capillaries of an observer, said apparatus comprising:

a source of illumination disposed in spaced relation to the observer;

filter means disposed between said source of illumination and the observer, said filter means being adapted to restrict the wavelength of light reaching the observer from said source of illumination to a predetermined wavelength such that the observer will experience the blue field entoptic phenomenon and thereby entoptically observe leukocytes in the retinal capillaries of that observer; and display means for displaying a plurality of simulated leukocytes, said display means being disposed between said source of illumination and said observer such that said simulated leukocytes are observed simultaneously with, and in the same visual field as, said entoptically observed leukocytes, said display means comprising additional means operable by the observer for adjusting the number and speed and pulsatility of said simulated leukocytes displayed on said display means, whereby the observer can compare said entoptically observed leukocytes with said simulated leukocytes so as to determine the number and speed and pulsatility of said entoptically observed leukocytes.

13. Apparatus according to claim 12 wherein a moving artificial pupil is disposed between said light source and the observer, whereby the observer will experience the Perkinje effect.

14. Apparatus according to claim 12 wherein said apparatus further comprises means for selectively interrupting light reaching the observer from said light source, whereby the observer will experience the flicker effect of the blue field entoptic phenomenon.

15. Apparatus according to claim 12 wherein said display means are further adapted to display a circle of variable size such that said circle is observed simultaneously with, and in the same visual field as, said entoptically observed leukocytes, and further wherein said display means comprise further means operable by the observer for adjusting the size of said circle, whereby the observer can compare that observer's entoptically observed foveal avascular zone with said circle so as to determine the size of said foveal avascular zone.

* * * * *